United States Patent
Wenzel

(10) Patent No.: US 11,065,657 B1
(45) Date of Patent: Jul. 20, 2021

(54) COMPOSITIONS AND METHODS FOR OXIDIZING AND SEQUESTERING CARBON AND STABILIZING METALS

(71) Applicant: Andrew Wenzel, Mount Horeb, WI (US)

(72) Inventor: Andrew Wenzel, Mount Horeb, WI (US)

(73) Assignee: URSUS REMEDIATION TESTING & TECHNOLOGIES, LLC, Mount Horeb, WI (US)

( * ) Notice: Subject to any disclaimer, the term of this patent is extended or adjusted under 35 U.S.C. 154(b) by 530 days.

(21) Appl. No.: 15/922,491

(22) Filed: Mar. 15, 2018

Related U.S. Application Data

(60) Provisional application No. 62/473,836, filed on Mar. 20, 2017.

(51) Int. Cl.

| | |
|---|---|
| *B09C 1/08* | (2006.01) |
| *C01B 32/60* | (2017.01) |
| *A62D 3/38* | (2007.01) |
| *C01B 15/08* | (2006.01) |
| *C07C 69/96* | (2006.01) |
| *C01F 11/18* | (2006.01) |

(52) U.S. Cl.
CPC ............ *B09C 1/08* (2013.01); *A62D 3/38* (2013.01); *C01B 15/08* (2013.01); *C01B 32/60* (2017.08); *C07C 69/96* (2013.01); *B09C 2101/00* (2013.01); *C01F 11/18* (2013.01)

(58) Field of Classification Search
CPC ....... B09C 1/08; B09C 2101/00; C07C 69/96; C01B 15/08; C01B 32/60; A62D 3/38; C01F 11/18
See application file for complete search history.

(56) References Cited

U.S. PATENT DOCUMENTS

| | | |
|---|---|---|
| 4,181,652 A | 1/1980 | Detroit |
| 4,274,969 A | 6/1981 | Lecoq et al. |
| 4,741,833 A | 5/1988 | Sheikh |
| 5,037,479 A | 8/1991 | Stanforth |
| 5,104,550 A | 4/1992 | Stevens et al. |
| 5,202,033 A | 4/1993 | Stanforth |
| 5,849,201 A | 12/1998 | Bradley |
| 6,019,548 A | 2/2000 | Hoag et al. |
| 6,254,312 B1 | 7/2001 | Chowdhury et al. |
| 6,268,205 B1 | 7/2001 | Kiest et al. |
| 6,543,964 B2 | 4/2003 | Chowdhury et al. |
| 6,768,205 B2 | 7/2004 | Taniguchi et al. |
| 6,843,617 B2 | 1/2005 | Chowdhury et al. |
| 7,204,929 B2 | 4/2007 | Fulconis et al. |
| 7,524,141 B2 | 4/2009 | Sethi et al. |
| 7,576,254 B2 | 8/2009 | Block et al. |
| 7,828,974 B2 | 11/2010 | Scalzi |
| 8,147,694 B2 | 4/2012 | Scalzi et al. |
| 9,126,245 B2 | 9/2015 | Scalzi et al. |
| 9,221,669 B2 | 12/2015 | Tix et al. |
| 2007/0280785 A1* | 12/2007 | Block .................... C02F 1/725 405/128.55 |

OTHER PUBLICATIONS

Bossmann SH, Oliveros E, Gob S, Siegwart S, Dahlen EO, Payawan L, Straub M, Worner M, Braun AM. 1998. New evidence against hydroxyl radicals as reactive intermediates in the thermal and photochemically enhanced Fenton reaction. J Phys Chem A 102:5542-5550.
Buxton GV, Greenstock CL, Helman WP, Ross AB. 1988. Critical reviews of rate constants for reactions of hydrated electrons, hydrogen atoms and hydroxyl radicals (•OH/•O-) in aqueous solution. J Phys Chem Ref Data 17:513-886.
Chenju Liang, Zih-Sin W, Nihar M. 2006. Influences of carbonate and chloride ions on persulfate oxidation of trichloroethylene at 20 ° C. Sci of the Tot Environment. 370: 271-277.
House DA. 1962. Kinetics and mechanism of oxidations by peroxydisulfate. Chem Rev 62:185-203.
Huie RE, Clifton CL, Neta P. 1991. Electron transfer reaction rates and equilibria of the carbonate and sulfate radical anions. Int J Rap Appl Instrum C Radiat Phys Chem 38:477-481.
Huling SG, Arnold, RG, Sierka RA, Miller MR. 1998. Measurement of hydrowyl radical activity in a soil slurry using the spin trap a-(4-Pyridyl-1-oxide)-N-tert-butylnitrone. Environ. Sci. Technology 32: 3436-3441.
Kolthoff IM, Miller IK. 1951. The chemistry of persulfate. I. The kinetics and mechanism of the decomposition of the persulfate ion in aqueous medium. J Am Chem Soc 73:3055-9.
Liang CJ, Huang SC. 2012. Kinetic model for sulfate/hydroxyl radical oxidation of methylene blue in a thermally-activated persulfate system at various pH and temperatures. Sustain. Environ. Res., 22(4), 199-208.
Neta P, Madhavan V, Zemel H, Fessenden R. 1977. Rate constants and mechanism of reaction of SO4—with aromatic compounds. J Am Chem Soc 99:163-4.
Satoh AY, Trosko, JE, Masten, SJ. 2007. Methylene Blue Dye Test for Rapid Qualitative Detection of Hydroxyl Radicals Formed in a Fenton's Reaction Aqueous Solution. Environ. Sci. Technology 41: 2881-2887.
Siegrist R.L., Crimi, M., and Simpkin, T.J. In-Situ Chemical Oxidation for Groundwater Remediation. Springer Science + Business Media. 2011, p. 348.

(Continued)

*Primary Examiner* — Daniel C. McCracken
(74) *Attorney, Agent, or Firm* — Daniel A. Blasiole; DeWitt LLP

(57) ABSTRACT

Compositions and methods for oxidizing organic contaminants while sequestering inhibitory forms of carbon. An oxidant capable of producing free radicals oxidizes organic contaminants. A metal oxide, metal hydroxide, or metal peroxide generates a soluble hydroxide concentration of about $1 \times 10^{-4}$ M or greater to convert carbonic acid, bicarbonate ion, methane, elemental carbon, and other organic forms of carbon to carbonate ion. A metal having a carbonate with a lower solubility product constant than its hydroxide precipitates the carbonate ion as a metal carbonate, thereby eliminating soluble carbonate as a radical scavenger. Compositions and methods that additionally minimize metal solubilization and sequester solubilized metals are also disclosed.

44 Claims, 2 Drawing Sheets

(56) References Cited

OTHER PUBLICATIONS

Staehelin J, Hoigné J. 1982. Decomposition of ozone in water: Rate of initiation by hydroxide ions and hydrogen peroxide. Environ. Sci. Technology 16: 676-681.

Wenzel, AD. 2012. Influence of ISCO Catalysts, Activators, and Chelators on Secondary Metals Mobility in Soil & Groundwater. Re3 Conference, Nov. 13, 2012.

Zuo Z, Cai Z, Katsumura Y, Chitose N, Muroya Y. 1999. Reinvestigation of the acid-base equilibrium of the (bi)carbonate radical and pH dependence of its reactivity with inorganic reactants. Radiat Phys Chem 55:15-23.

Haselow, J, S., Siegrist, R, L., Crimi, M., and Jarosch, T. 2003. Estimating the Total Oxidant Demand for in Situ Chemical Oxidation Design. Remediation Autumn 2003. pp. 5-16.

Krembs, FJ. 2008. Critical Analysis of the Field-Scaled Application of in Situ Chemical Oxidation for the Remediation of Contaminated Groundwater. MS Thesis, Colorado School of Mines, Golder CO. pp. 93-95.

Lee H, A Park, Colin O. 2000. Stability of hydrogen peroxide in sodium carbonate solutions. TAPPI J. Peer Review Paper. pp. 1-9.

*CRC Handbook of Chemistry and Physics*, 84th Ed.; Lide, D.R., Ed.; CRC Press: Boca Raton, FL, 2003; Section 3, pp. 8-23 and 8-24.

Mehrab M, Anderson W, Murray M., 2001. Photocatalytic degradation of aqueous organic solvents in the presence of hydroxyl radical scavengers. Inter. J. of Photoenergy 3:187-191.

Osgerby IT. 2011. Site Characterization for ISCO Projects. NEWMOA Workshop, Mar. 15, 2011. http://www.newmoa.org/cleanup/cwm/isco/pres/Ogersby.pdf pp. 2-32.

PeroxyChem. Activating Klozur® SP with a 25% Sodium Hydroxide Solution. 2012. http://www.peroxychem.com/media/191078/peroxychem-klozur-sp-activation-guide-alkaline-25.pdf. pp. 1-3.

* cited by examiner

COMPOSITIONS AND METHODS FOR OXIDIZING AND SEQUESTERING CARBON AND STABILIZING METALS

FIELD OF THE INVENTION

The invention is directed to oxidizing carbon and sequestering the oxidized carbon. In some versions, the invention is further directed to minimizing metal mobilization during the carbon oxidation while stabilizing mobilized or contaminating metals.

BACKGROUND

Chemical oxidation using free radicals is widely used for degrading or mineralizing organic contaminants. Chemical oxidation is effective on volatile organic compounds, semivolatile organic compounds, non-halogenated and halogenated solvents, polyaromatic hydrocarbons, total petroleum hydrocarbons, polychlorinated biphenyls, chlorinated benzenes, gasoline additives, pesticides, and other organic contaminants.

The effectiveness of chemical oxidation using free radicals is greatly influenced by the presence of bicarbonate ($HCO_3^-$) and carbonate ($CO_3^{-2}$). Bicarbonate and carbonate are known to scavenge various forms of free radicals, including hydroxide and sulfate radicals, by converting them into carbonate radicals. Carbonate radicals are strong oxidizers (1.59V), but not as strong as other radicals such as hydroxyl radicals (2.59V) and sulfate radicals (2.43V) (see Table 2 in the Examples). Some contaminants are effectively mineralized with bicarbonate and carbonate radicals, but, overall, bicarbonate and carbonate ions and their respective radicals have a negative impact on free radicals primarily responsible for contaminant degradation. The presence of bicarbonate and carbonate ions therefore reduces the effectiveness of chemical oxidation, requiring addition of excess oxidant and/or a longer treatment period to achieve contaminant degradation. In some cases, contaminant degradation stops altogether, regardless of the amount of oxidant added or longevity of treatment.

Bicarbonate and carbonate ions are pervasive in soil and groundwater. Sources of bicarbonate and carbonate ions include atmospheric contributions; natural mineralization of organic compounds, including natural organic matter and soil; and chemical degradation of organic compounds with oxidants. Of particular importance is the oxidant-mediated mineralization of organic compounds to carbon dioxide, which then forms bicarbonate and carbonate under alkaline conditions. Systems that have initially low concentrations of bicarbonate and/or carbonate can see bicarbonate and carbonate build to levels that affect oxidation efficiency as mineralization of organic compounds occurs. Systems with high calcareous formations (limestone) are particularly prone to carbonate and bicarbonate inhibition. In most cases, acid adjustment to a low pH is not practical due to the amount of acid required to achieve the target pH and the great quantity of carbon dioxide gas released. Systems that undergo anaerobic decomposition are also particularly prone to carbonate and bicarbonate inhibition. Anaerobic decomposition produces reduced forms of carbon such as methane. When an oxidant is added at pH levels greater than about 10, methane will oxidize to inorganic carbon and be converted to carbonate ion via bicarbonate ion.

Chemical additives that are used to make contaminates more readily accessible to oxidation may impede the performance of the oxidant by forming bicarbonate and carbonate. Activated carbon and materials containing activated carbon, for example, are additives used to adsorb contaminants, making them more readily available to treatment. After contaminant adsorption by activated carbon, an oxidant can be used to mineralize the contaminant. During oxidation, activated carbon is also oxidized, converting the activated carbon to ionic forms of carbon. Depending on the pH of the system, carbon dioxide, bicarbonate, carbonate, and combinations thereof can form. As outlined above, the formation or bicarbonate and carbonate impedes oxidant performance. Surfactants are additives used to desorb organic compounds from substrates to make them more water soluble and susceptible to oxidation. Surfactants are long carbon chains that can be oxidized by oxidants Similar to other organic carbon, natural organic matter, and organic contaminants, oxidation of surfactants builds inorganic carbon in the system to levels that affect oxidant efficiency.

Compositions and methods that address the inhibitory effect of bicarbonate and carbonate on chemical oxidation of organic contaminants are needed.

A secondary effect of chemical oxidation is the mobilization or solubilizing of naturally occurring or anthropogenic metals. Mixed wastes that contain both organic and metals contamination are of particular concern. Organic contaminated sites that do not have groundwater metal regulatory concerns may, after oxidant treatment with an activator or catalyst, observe a significant increase in groundwater metals concentrations. Metals that are stable in a system and pose no immediate regulatory concern can be mobilized by the activator or catalyst, thereby creating secondary contamination.

Oxidants can mobilize stable forms of metals to more soluble forms. For example, redox sensitive metals such as Cr(III) can be converted to Cr(VI), where Cr(VI) is very soluble and can mobilize to groundwater. Additionally, PbS can be oxidized to $PbSO_4$, which is very soluble. The activation method for the oxidants can also mobilize metals. The activator or catalyst can increase dissolved metals concentrations by changing the pH of the system or by adding a chelating agent. Metal catalysts such as iron, for example, are commonly used to activate hydrogen peroxide (Fenton's Reaction) and persulfate. The catalyst needs to be in a soluble form to favor a catalytic reaction. Adjustment of the substrate with acid to a pH of 3-5 is commonly applied to maintain iron solubility. The low pH not only maintains the solubility of iron but also mobilizes metals from the substrate. Metal chelators have also been applied to maintain solubility of the metal catalyst at a neutral pH. The metal chelator complexes metals from the substrate, causing unwanted or regulated metals to increase in concentration. Oxidation of soil organic matter can also increase metals mobilization by degrading soil organic matter that complexes or adsorbs metals. Depending on the oxidant and method of activation, metals from the substrate can dissolve, creating a secondary contamination concern.

Compositions and methods that efficiently oxidize carbon while minimizing metal contamination are needed.

SUMMARY OF THE INVENTION

The present invention addresses the aforementioned needs by providing compositions and methods for oxidizing organic contaminants while sequestering inhibitory forms of carbon. An oxidant capable of producing free radicals oxidizes organic contaminants. A metal oxide, metal hydroxide, or metal peroxide generates a soluble hydroxide concentration of about $1 \times 10^{-4}$ M or greater to convert carbonic acid, bicarbonate ion, methane, elemental carbon, and other organic forms of carbon to carbonate ion. A metal having a carbonate with a lower solubility product constant than its hydroxide precipitates the carbonate ion as a metal carbonate, thereby eliminating soluble carbonate as a radical scavenger.

The present invention addresses the aforementioned needs also by providing compositions and methods that minimize metal solubilization and sequester solubilized metals. Certain versions of the present invention employ hydroxide concentrations near $1 \times 10^{-4}$ M, which minimize secondary metal mobilization from substrate. Stabilizing agents such as phosphate, iron, and manganese stabilize any metals that are mobilized. Sulfate further stabilizes metals if the system becomes anoxic/reduced after oxidation whereby sulfate is reduced to sulfide and metals are precipitated as metal sulfides. Phosphates and/or nitrogen serve as nutrients to facilitate biologically driven anaerobic conditions.

The above-mentioned reagents are included in compositions and employed in methods of the invention.

The methods described herein are useful to treat soil/groundwater to meet contaminant regulatory requirements, treat wastes so they are deemed nonhazardous for proper disposal, and other uses.

The objects and advantages of the invention will appear more fully from the following detailed description of the preferred embodiment of the invention made in conjunction with the accompanying drawings.

DETAILED DESCRIPTION OF THE INVENTION

Figure 1:
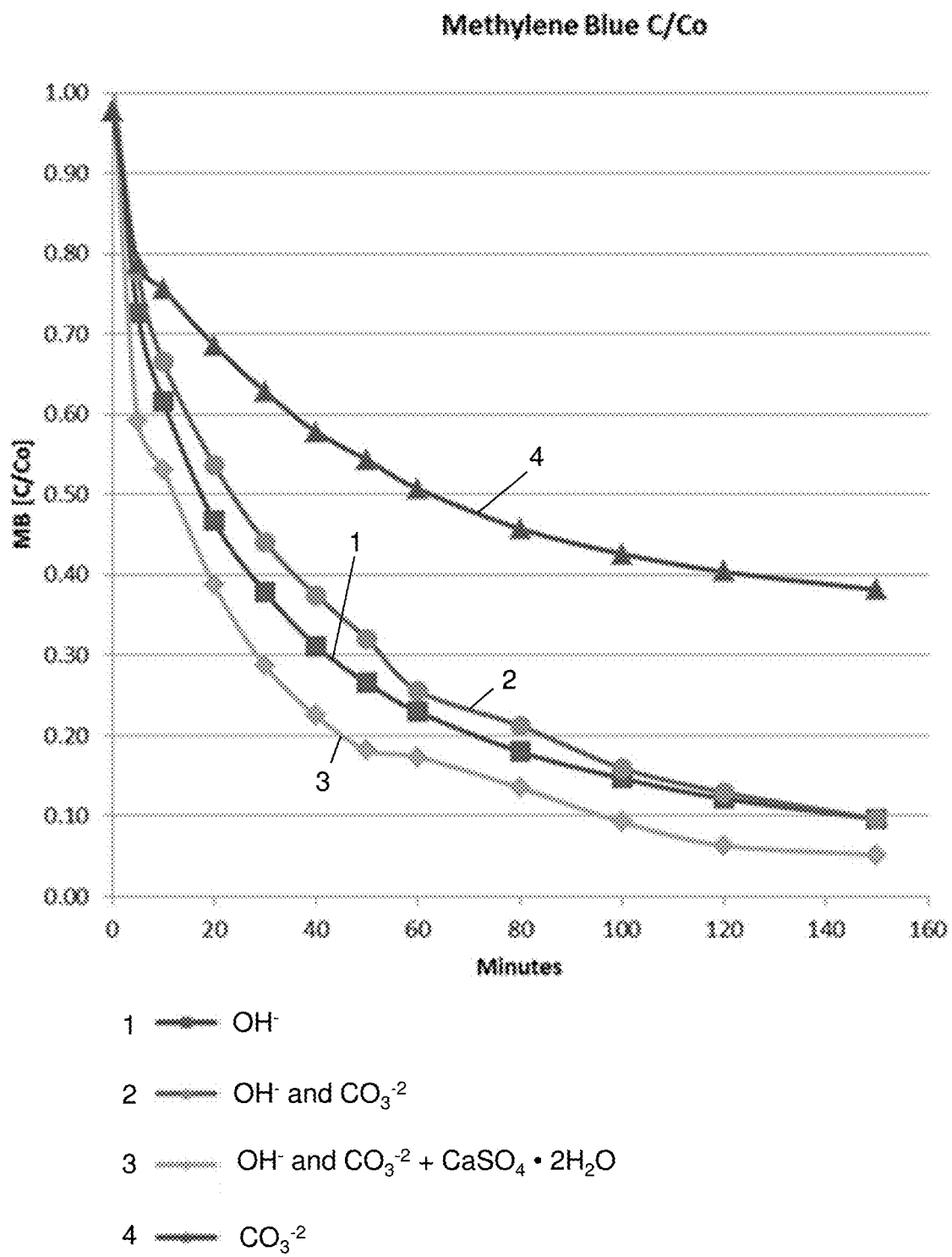
FIG. 1 shows degradation of methylene blue (MB) with varying alkaline activation conditions for oxidants. The conditions are $OH^-$ as a sole alkaline agent, $OH^-$ and $CO_3^{-2}$ as alkaline agents, $OH^-$ and $CO_3^{-2}$ as alkaline agents in combination with a calcium salt ($CaSO_4+2H_2O$), and $CO_3^{-2}$ as a sole alkaline agent. The oxidant in all conditions is sodium persulfate (SPS). For all Experiments, $[SPS]=7.37 \times 10^{-3}$ M, $[MB]=1.61 \times 10^{-5}$ M, $[OH^-]=1.74 \times 10^{-2}$ M, $[CO_3^{-2}]=1.98 \times 10^{-2}$ M, $[CaSO_4+2H_2O]=3.78 \times 10^{-2}$ M.

One aspect of the invention comprises methods of oxidizing carbon in a substrate. The carbon may be in the form of inorganic carbon or organic carbon. The inorganic carbon includes elemental carbon, such as activated carbon. The organic carbon may include any organic compound capable of being oxidized. The organic compound may be a contaminant, such as an environmental contaminant, or an organic compound used to enhance the ability of the oxidant to oxidize the contaminant. Organic compounds used to mobilize environmental contaminants and enhance the performance of the oxidant include surfactants. The surfactants may include anionic, cationic, and/or nonionic surfactants. The organic compound may be carcinogenic or toxic. Exemplary types of organic compounds that can be oxidized by the methods of the present invention include but are not limited to volatile organic compounds (VOCs); semi volatile organic compounds (SVOCs); non-halogenated solvents; halogenated solvents; polychlorinated biphenyls (PCBs); polyaromatic hydrocarbons (PAHs); chlorinated benzenes; total petroleum hydrocarbons (TPHs) including benzene, toluene, xylene and ethylbenzene; methyl t-butyl ether (MTBE); brominated solvents; 1,4-dioxane; gasoline additives; and pesticides (insecticides, herbicides, etc.); perfluorinated chemicals, haloalkanes (PFOA, PFOS, etc.), and explosives. Exemplary organic compounds that can be oxidized by the methods of the present invention include but are not limited to chlorinated solvents such as trichloroethylene (TCE), vinyl chloride, tetrachloroethylene (PCE), methylene chloride, 1,2-dichloroethane, 1,1,1-trichloroethane (TCA), 1,1-dichloroethane, 1,1-dichloroethene, carbon tetrachloride, benzene, chloroform, chlorobenzenes, and other compounds such as ethylene dibromide, and methyl tertiary butyl ether.

The carbon to be oxidized may be present in a substrate. The substrate may comprise any medium containing the carbon. The substrate may comprise liquid, solid, or a combination of liquid and solid. The substrate preferably comprises an aqueous substrate. The substrate may be an environmental medium. Exemplary environmental media include but are not limited to soil, rock, groundwater, plumes, aquifers, process water, waste water, and the like. The substrate may be a human-made medium. An exemplary human-made medium includes but is not limited to hazardous waste or other contaminated materials submerged in a solvent, such as an aqueous solvent.

The organic carbon may be oxidized by treating the substrate with an oxidant capable of producing free radicals in an amount sufficient to oxidize the organic carbon in the substrate. The contacting may occur through treating the substrate with the oxidant. Oxidants capable of producing free radicals include persulfate, hydrogen peroxide, ozone, percarbonate, or any combination thereof. The oxidants can be activated to produce free radicals by any suitable method. Exemplary activation methods are described in further detail herein. A preferred mechanism of activation is alkaline activation. Alkaline activation in combination with ultraviolet (UV) activation is also suitable. The addition of heat can enhance the activation of oxidants such as persulfate under alkaline conditions.

Among persulfates, any solid phase water soluble persulfate compound can be used as the oxidant, including monopersulfates, dipersulfates, and combinations thereof. Exemplary dipersulfates include sodium persulfate, potassium persulfate, ammonium persulfate, and combinations thereof. Exemplary monopersulfates include sodium monopersulfate, potassium monopersulfate, and combinations thereof.

In some versions of the invention, permanganate is used in combination with the oxidant capable of producing free radicals, such as any one or more of persulfate, hydrogen peroxide, ozone, and percarbonate. The permanganate is a source of manganese, which is useful for stabilization of metals by adsorption, as a pH control for amphoteric metals, and as an electron acceptor for bioremediation.

In some versions, persulfate, either alone or in combination with permanganate, is preferred as it provides a source of sulfate and manganese as an electron acceptor for microbes and sulfide for precipitating contaminating metals.

For alkaline activation, the substrate preferably has a hydroxide concentration of at least about $1 \times 10^{-4}$ M, such as at least about $5 \times 10^{-4}$ M, at least about $1 \times 10^{-3}$ M, at least about $5 \times 10^{-3}$ M, or at least about $1 \times 10^{-2}$ M. The substrate is preferably at a pH of at least about 9, such as at least about 9.5, at least about 10, at least about 10.5, at least about 11, at least about 11.5, at least about 12, at least about 12.5, or at least about 13. These pHs are also effective to shift the form of inorganic carbon in the system from carbonic acid to bicarbonate to carbonate ion (see eqs. 17 and 18 below) for precipitation of carbonate ion from the substrate.

Some versions of the invention avoid extremely high hydroxide concentrations and/or pH levels in order to prevent or minimize mobilization of metals, such as amphoteric metals, into the substrate. In such versions, the hydroxide concentration is preferably no greater than about $1\times10^{-2}$ M, such as no greater than about $5\times10^{-3}$ M, no greater than about $1\times10^{-3}$ M, or no greater than about $5\times10^{-4}$ M. Exemplary hydroxide concentration ranges include from about $1\times10^{-4}$ M to about $1\times10^{-2}$ M, from about $1\times10^{-4}$ M to about $5\times10^{-3}$ M, from about $1\times10^{-4}$ M to about $1\times10^{-3}$ M, or from about $1\times10^{-4}$ M to about $5\times10^{-4}$ M. The pH in such versions is preferably no greater than about 12, such as no greater than about 11.5, no greater than about 11, or no greater than about 10.5. Exemplary pH ranges include from about 10 to about 12, from about 10 to about 11.5, from about 10 to about 11, or from about 10 to about 10.5.

At hydroxide concentrations near $1\times10^{-4}$ M and pH levels near 10, bacterial populations are less stressed and a decline in populations is minimized. At higher hydroxide concentrations and pH levels, bacterial populations in the substrate are shocked, causing a lag period before populations recover.

The targeted hydroxide and pH levels for alkaline activation may be obtained by treating the substrate with a metal oxide, hydroxide, or peroxide in an amount sufficient to yield a total hydroxide concentration of about $1\times10^{-4}$ M or greater in the substrate. Metal oxides, hydroxides, or peroxides are referred to herein as "alkaline agents." The metal in the metal oxide, hydroxide, or peroxide may comprise any Group 1 metal (e.g., lithium, sodium, potassium, etc.), calcium, strontium, barium, magnesium, manganese, combinations thereof (e.g., calcium magnesium oxide, CaOMgO, Portland Cement/Portland Cement that contains or has gypsum added ($CaSO_4$), and hydrates thereof), or others. In some versions, oxides, hydroxides, or peroxides of calcium, strontium, or barium are preferred to provide a source of a metal suitable for precipitating carbonate ion from the substrate. In some versions, oxides, hydroxides, or peroxides of magnesium or manganese (e.g., magnesium oxide (MgO), magnesium hydroxide ($Mg(OH)_2$), magnesium peroxide ($MgO_2$), manganese(II) oxide (MnO), manganese(II,III) oxide ($Mn_3O_4$), manganese(III) oxide ($Mn_2O_3$), manganese dioxide (manganese(IV) oxide) ($MnO_2$), manganese(VI) oxide ($MnO_3$), manganese(VII) oxide ($Mn_2O_7$)) are preferred to prevent or minimize mobilization of metals in the substrate. $Mg(OH)_2$, for example, yields a hydroxide concentration of $2.24\times10^{-4}$ at saturation, and $Mn(OH)_2$ yields a hydroxide concentration of $7.49\times10^{-5}$ at saturation. These hydroxide concentrations fulfill the criterion of being "about $1\times10^{-4}$ M" as used herein. At these hydroxide concentrations, amphoteric metal mobilization is minimal while still providing a hydroxide concentration capable of alkaline activating the oxidant. In some versions, permanganate ion is used as an oxidant and is combined with an alkaline agent at stoichiometric amounts to produce $Mn(OH)_2$ in situ.

In order to precipitate carbonate from the substrate, the substrate is treated with a metal whose carbonate has a lower solubility product constant than its hydroxide, such that the presence of the metal in the substrate preferentially precipitates carbonate ions over hydroxide ions. Metals whose carbonates have a lower solubility product constant than their respective hydroxides are referred to herein as precipitating metals. The solubility product constant ($K_{sp}$) is the equilibrium constant for a solid substance dissolving in an aqueous solution. It represents the level at which a solute dissolves in solution. The more soluble a substance is, the higher the $K_{sp}$ value it has. An example for determining $K_{sp}$ can be demonstrated with the general dissolution reaction below (in aqueous solution):

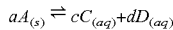

To solve for Ksp, the molarities or concentrations of the products (cC and dD) are multiplied. If there are coefficients in front of any of the products, the product is raised to that coefficient power (and the concentration is also multiplied by that coefficient), as shown below:

$$K_{sp}=[C]^c[D]^d$$

Hence, $K_{sp}$ represents the maximum extent that a solid that can dissolve in solution.

Exemplary precipitating metals include alkaline earth metals, such as calcium, strontium, and barium. The $K_{sp}$ of calcium carbonate is $5.0\times10^{-9}$, and the $K_{sp}$ of calcium hydroxide is $4.7\times10^{-6}$. The $K_{sp}$ of strontium carbonate is $5.6\times10^{-10}$, and the $K_{sp}$ of strontium hydroxide is $6.4\times10^{-3}$. The $K_{sp}$ of barium carbonate is $5.1\times10^{-9}$, and the $K_{sp}$ of barium hydroxide is $5.0\times10^{-3}$.

Precipitating metals can be added to the substrate in any form in which the precipitating metal at least partially dissolves in the substrate. The precipitating metals can be added in their oxide, hydroxide, peroxide or salt forms. The term "salt" as used herein explicitly excludes oxides, hydroxides, and peroxides but is otherwise used as commonly understood in the art. As commonly understood in the art, the term "salt" includes both hydrates and non-hydrates.

The precipitating metal is preferably added to the substrate in an amount sufficient to maintain, preferably through the entire duration of the oxidation process, a concentration of an ionic form of the first metal in the substrate equal to or greater than a concentration of bicarbonate and carbonate ions in the substrate. This provides sufficient amounts of the metal to precipitate carbonate ion. The precipitating metal is preferably added to the substrate in an amount sufficient to maintain, preferably through the entire duration of the oxidation process, a free hydroxide concentration greater than the free carbonate and/or bicarbonate ion concentration. This provides alkalinity primarily in a hydroxide rather than carbonate form, and provides sufficient hydroxide ions for formation of free radicals with high oxidation potential.

In some substrates, precipitating metals can be added solely in their oxide, hydroxide, and/or peroxide forms. However, precipitating metals in these forms can be limiting for precipitating carbonate. Thus, preferred versions of the invention comprise adding one or more salts of a precipitating metal. The salt of the precipitating metal can be a neutral salt, a basic salt, or an acidic salt, but neutral and basic salts are preferred. Neutral salts are salts that are the product of the neutralization of a strong acid and a strong base. Basic salts are salts that are the product of the neutralization of a strong base and a weak acid. Acidic salts are salts that are the product of the neutralization of a weak base and a strong acid.

The counterion in the salt of the precipitating metal can be any counterion. Exemplary counterions include but are not limited to acetate, arsenide, azide, benzoate, bromide, butyrate, carbide, chlorate, chromate, chloride, chlorite, citrate, cyanamide, cyanate, cyanide, dichromate, dihydrogen phosphate, fluoride, formate, gluconate, lactate, hydrogen sulfate, hydrogen sulfide, hydride, hypochlorite, lactate, glycerophosphate, isocyanate, iodate, iodide, monohydrogen phosphate, nitrate, nitride, nitrite, oxalate, perchlorate, permanganate, phosphate, phosphide, phosphite, propionate, selenide, silicate, sulfate, sulfide, sulfite, thiocyanate, and thiosulfate. In some versions of the invention, sulfate, sulfide, phosphate, and silicate counterions are preferred for their amphoteric metal sequestration properties.

Exemplary salt forms of calcium that can be added to the substrate include but are not limited to calcium acetate ($Ca(C_2H_3O_2)_2$), calcium bromide ($CaBr_2$), calcium benzoate ($Ca(C_7H_5O_2)_2$), calcium butyrate ($Ca(C_4H_7O_2)_2$), calcium chloride ($CaCl_2$), calcium citrate ($Ca_3(C_6H_5O_7)_2$), calcium cyanamide (CaNCN), calcium fluoride ($CaF_2$), calcium fluorophosphate dehydrate ($CaFPO_3.2H_2O$), calcium formate ($Ca(HCO_2)_2$) calcium hydride ($H_2Ca$), calcium gluconate ($C_{12}H_{22}CaO_{14}$), calcium iodate ($Ca(IO_3)_2$), calcium iodide ($CaI_2$), calcium lactate ($C_6H10CaO6$), calcium nitrate ($Ca(NO_3)_2$,), calcium nitrite ($Ca(NO_2)_2$), calcium oxalate ($CaC_2O_4$), calcium permanganate ($Ca(MnO_4)_2$) calcium perchlorate ($Ca(ClO_4)_2$), calcium phosphate tribasic ($[Ca_5(OH)(PO_4)_3]_x$), calcium phosphate monobasic ($Ca(H_2PO_4)_2$), calcium pyrophosphate ($Ca_2P_2O_7$), calcium propionate $Ca(C_2H_5COO)_2$ calcium sulfate ($CaSO_4$), calcium thiocyanate $Ca(SCN)_2$), hydroxyapatite ($[Ca_5(OH)(PO_4)_3]_x$), triple superphosphate (TSP) ($Ca(H_2PO_4)_2.H_2O$), fluorapatite ($Ca_5(PO_4)_3F$), hydroxyapatite ($Ca_5(PO_4)_3OH$), and hydrates of any of the above, among others.

When a salt of a precipitating metal is added to the substrate, the metal in the alkaline agent can include the same metal or a different metal. For example, if calcium sulfate is added as a precipitating metal, the alkaline agent can include calcium oxide, hydroxide, or peroxide or an oxide, hydroxide, or peroxide of a metal other than calcium. Metals other than the precipitating metal that can be included in the alkaline agent include Group 1 metals, magnesium, and/or manganese. Including magnesium and/or manganese in the alkaline agent is preferred for controlling release of amphoteric metals.

The salt of the precipitating metal is preferably stoichiometrically added to the substrate in excess of the bicarbonate and carbonate ions in the substrate at any given time. This provides sufficient amounts of the metal to precipitate carbonate ion. The salt of the precipitating metal is preferably added to the substrate in an amount sufficient to maintain a free hydroxide concentration greater than the free carbonate and/or bicarbonate ion concentration. This provides alkalinity primarily in a hydroxide rather than carbonate form, and provides sufficient hydroxide ions for formation of free radicals with high oxidation potential.

In some versions of the invention, treating the substrate can involve adding two or more separate compositions to it. Each separate composition preferably comprises a separate set of chemicals therein. Such versions can be advantageous when one or more of the agents used to treat the substrate are insoluble or only slightly soluble in aqueous solution and form a slurry therein. Such slurries can cause problems with regard to storage and delivery in a consistent manner. Instead of adding pre-formed insoluble or slightly soluble compounds directly to the substrate, precursors of the compounds are added in separate solutions such that the effective agents are formed in situ.

For example, alkaline agents containing calcium, strontium, barium, magnesium, and manganese, such as hydroxides thereof, are only slightly soluble in water. These alkaline agents therefore form slurries in aqueous solution, making it difficult to appropriately deliver these alkaline agents to the substrate. Instead (or in addition to) adding these alkaline agents directly to a substrate, they can be generated in situ by adding a calcium, strontium, barium, magnesium, or manganese salt in a first composition and adding a readily soluble metal oxide, hydroxide, or peroxide in a second, separate composition. Calcium, strontium, barium, magnesium, or manganese hydroxide will form when the two compositions mix in situ. ("Or" in this case is used in an inclusive manner. Thus, any combination of calcium, strontium, barium, magnesium, or manganese salts can be added together in the first composition, and any combination of metal oxides, hydroxides, and peroxides can be added together in the second composition.)

In versions of the invention in which the first and second composition are added, the calcium, strontium, barium, or magnesium is preferably added in an amount greater than a stoichiometric amount to form a hydroxide from the metal oxide, hydroxide, or peroxide thereof in the second composition. In the case of calcium, strontium, or barium, this provides sufficient amounts of these precipitating metals to precipitate carbonate from the substrate. In the case of magnesium, this ensures that magnesium is not limiting, thereby ensuring control of substrate alkalinity to prevent or minimize amphoteric metal mobilization.

The counterion for the calcium, strontium, barium, or magnesium salt in the first composition can comprise any counterion described herein. In some versions of the invention, sulfate, sulfide, phosphate, and silicate counterions are preferred for their metal stabilization properties. Exemplary salts of calcium include any of those provided herein. Exemplary salts of magnesium include magnesium chloride ($MgCl_2$), magnesium sulfate heptahydrate ($MgSO_4.7H_2O$), magnesium phosphate ($Mg(H_2PO_4)_2$), dimagnesium phosphate ($MgHPO_4$), potassium magnesium sulfate ($K_2SO_4.O.2MgSO_4$), magnesium phosphate tribasic ($Mg_3(PO_4)_2$), amorphous magnesium phosphate, and hydrates of any of the above, among others.

While the second composition may comprise at least some oxides, hydroxides, or peroxides of a metal that are provided in salt form in the first composition, the second composition preferably comprises at least one oxide, hydroxide, peroxides of a metal that is different than a metal provided in salt form in the first composition. The metal oxide, hydroxide, or peroxide in the second composition preferably comprises a Group 1 metal, such as lithium, sodium, etc.

The oxidant and any other components used to treat the substrate, such as metal stabilizing agents, etc., can be included in the first composition, the second composition, or one or more separate compositions in addition to the first and second compositions.

The substrate can be treated with the first and second composition simultaneously or sequentially, wherein the sequential treatments do not overlap in time. The substrate can be treated with the first composition first and with the second composition second, or vice versa.

In order to stabilize metals already dissolved in the system prior to the oxidation treatment or mobilized in the system during the oxidation treatment, the substrate may be treated with any of a number of stabilizing agents. Stabilizing agents such as phosphate salts, iron salts, manganese salts, and silicates can stabilize metals immediately after treatment where the condition of the system is oxidized and at a pH near 10. The stabilizing agents can be included as part of other agents discussed herein, such as the oxidant, alkaline agent, and/or precipitating salt, etc., or can constitute separate compounds in addition to these agents.

Phosphates from phosphate salts form very insoluble metal precipitates with both amphoteric and non-amphoteric metals. Suitable phosphate salts include phosphates of any of the metals described herein with respect to the alkaline agent, the precipitating salt, or any other reagent. Additional phosphate salts include superphosphate, triple superphosphate ($Ca(H_2PO_4)_2 \cdot H_2O$), monoammonium phosphate (MAP) ($NH_4H_2PO_4$), and diammonium phosphate (DAP) (($NH_4)_2PO_4$), sodium phosphate dibasic ($Na_2HPO_4 \cdot 2H_2O$), sodium phosphate monobasic ($NaH_2PO_4 \cdot 2H_2O$), phosphoric acid ($H_3PO_4$), phosphorite, fluorapatite ($Ca_5(PO_4)_3F$), hydroxyapatite ($Ca_5(PO_4)_3OH$), fish bones, and hydrates of any of the above, among others. Some phosphate sources also provide a precipitating metal such as calcium, strontium, or barium or any combination thereof.

Iron forms iron hydroxides at hydroxide concentrations near $1 \times 10^{-4}$ M that facilitate co-precipitation of heavy metals and provide adsorption sites for metals and metalloids, including As, Se and Sb. Iron can be provided as an iron salt comprising iron complexed with any of the anions described herein. Exemplary iron salts are ferrous sulfate ($FeSO_4$), ferric sulfate ($Fe_2SO4)_3$), ferrous chloride ($FeCl_2$), and ferric chloride ($FeCl_3$), and hydrates thereof. Iron can also be provided as an iron oxide or hydroxide. Exemplary iron oxides or hydroxides are iron (II) oxide (FeO), iron (III) oxide ($Fe_2O_3$), Fe(II,III) oxide ($Fe_3O_4$), iron (II) hydroxide, iron (III) hydroxide, and iron (III) oxide-hydroxide. Iron can also be provided as zero valent iron (ZVI).

Manganese forms manganese oxides/hydroxides at a hydroxide concentration near $1 \times 10^{-4}$ M. The hydroxides are insoluble and provide adsorption sites for metals and metalloids, including As, Se and Sb. Manganese can be provided in the form of permanganate as both an oxidant and manganese source for metal stabilization. Manganese can also be provided as a manganese salt. The manganese salts can comprise manganese complexed with any of the anions described herein. Exemplary manganese salts are manganese(II) chloride, manganese II sulfate ($MnSO_4 \cdot H_2O$), sodium permanganate ($NaMnO_4$), potassium permanganate ($KMnO_4$), calcium permanganate ($Ca(MnO_4)_2$), and hydrates of any of the above.

In addition to the above-mentioned stabilizing agents, hydroxide ion itself is effective in precipitating heavy metals. In particular, metals such as Pb, Zn, Al and other amphoteric metals form stable metal hydroxides at a hydroxide concentration near $1 \times 10^{-4}$ M.

After oxidation treatment, the system may go anaerobic after the oxidant is spent and biological conditions change such that bacteria utilize anions from the treatment or substrate itself to facilitate reducing conditions in the system. These bacteria can be important for further degrading organic chemicals in the substrate.

Phosphate is an essential nutrient for bacteria. Thus, any added phosphate can facilitate the growth of bacteria in the system. Some of the above mentioned chemicals (e.g., MAP, DAP) also include nitrogen, which can also facilitate bacterial growth.

Sulfate is a common electron acceptor for bioremediation. Sulfate can come from the oxidant (e.g., persulfate), from the precipitating salt (e.g., calcium, strontium, or barium sulfate), from a magnesium salt used to form the alkaline agent in situ (e.g., MgSO4.7H2O), from a salt used to precipitate metals (e.g., ferric sulfate), or from a salt distinct from any of these sources. Sulfate can also come from the substrate being treated or formed after oxidation, where reduced forms of substrate sulfur are oxidized to sulfate.

Iron, particularly ferric iron ($Fe^{3+}$), can be used as an electron acceptor as well as a co-precipitant and provide adsorption sites. Iron also provides a catalyst for oxidants to produce radicals that are effective in decomposing organic compounds. Iron is amphoteric so it will be more soluble at higher pH levels where it is available as a catalyst for oxidants.

As the system goes anaerobic, sulfate will be reduced to sulfide. Sulfides form very insoluble metal precipitates.

Prior oxidation methods that merely use persulfate as an oxidation agent may have sulfate available as an electron acceptor, but conditions of the substrate to stabilize metals via metal sulfides may never be achieved. First, metal sulfates are mostly soluble or have a solubility where the metal exceeds background or regulatory standards. Second, bacteria must be present to utilize sulfate as an electron acceptor. At extremely high pH levels, the bacterial populations will be significantly reduced, requiring a lag period for populations to return to levels that can use sulfate as an electron acceptor. This can take months to years to achieve. Meanwhile, amphoteric metals can be mobilized. Finally, the system must convert to an anaerobic state for sulfate to biologically reduce to sulfide. Essential nutrients and energy sources must be present to sustain and build bacterial populations. If they are not, the system will remain aerobic. Therefore, sulfate conversion to sulfide will not occur and amphoteric metals can mobilize.

Exemplary formulations suitable for carrying out the methods of the present invention are provided in Table 1. Each formulation can be enhanced with the addition of heat, carbon/activated carbon, and/or surfactants. Activated carbon can include granular activated carbon (GAC, >1 mm size), powdered activated carbon (PAC, <1 mm in size), charcoal, Biochar, Bamboo Charcoal, among others. Activated carbon also includes activated carbons that are enhanced by impregnating anions such as sulfur, iodine, and bromide, among others, and cations including aluminum, calcium, iron, manganese, lithium, silver and zinc, among others. Surfactants include sodium dodecyl benzenesulfonate (SDBS), sodium dodecyl sulfonate (SDS), sodium lauryl sulfate (SLS), sodium dodecyl diphenyl ether disulfonate (C12-MADS), sodium dioctyl sulfosuccinate (AOT), polyoxyethylene lauryl ether (Brij 35), polyoxyethylene octyl phenyl ether (Triton X-100), and polyoxyethylene (20) sorbitan monooleate (Tween 80), among others.

TABLE 1

Exemplary Formulations

| Form | Chemical | Alkaline Agent | $HCO_3^-/CO_3^{-2}$ Precipitation Agent | Metal Mobilization- Prevention Agent | Metal Stabilization Agent | $SO_4^{-2}$ Electron Acceptor | Essential Nutrient | Catalyst |
|---|---|---|---|---|---|---|---|---|
| 1 | CaO, Ca(OH)$_2$, CaO$_2$ | x | x | | | | | |
| 2 | CaO, Ca(OH)$_2$, CaO$_2$ CaSO$_4$ | x | x | | | x | | |

TABLE 1-continued

Exemplary Formulations

| Form | Chemical | Alkaline Agent | $HCO_3^-/CO_3^{-2}$ Precipitation Agent | Metal Mobilization-Prevention Agent | Metal Stabilization Agent | $SO_4^{-2}$ Electron Acceptor | Essential Nutrient | Catalyst |
|---|---|---|---|---|---|---|---|---|
| 3 | $Na_2O$, NaOH, $Na_2O_2$ | x | | | | | | |
|   | $CaSO_4$ | | x | | x | | | |
| 4 | CaO, $Ca(OH)_2$, $CaO_2$ | x | x | | | | | |
|   | $CaSO_4$ | | x | | | x | | |
|   | $FeSO_4$ | | | | | x | | x |
| 5 | $Na_2O$, NaOH, $Na_2O_2$ | x | x | | | | | |
|   | $CaSO_4$ | | x | | | x | | |
|   | $FeSO_4$ | | | | | x | | x |
| 6 | MgO, $Mg(OH)_2$, $MgO_2$ | x | | x | x | | | |
|   | $CaSO_4$ | | x | | | x | | |
| 7 | MgO, $Mg(OH)_2$, $MgO_2$ | x | | x | x | | | |
|   | $CaSO_4$ | | x | | | x | | |
|   | MAP/DAP | | | | x | | x | |
| 8 | MgO, $Mg(OH)_2$, $MgO_2$ | x | | x | x | | | |
|   | $CaSO_4$ | | x | | | x | | |
|   | MAP/DAP | | | | x | | x | |
|   | $FeSO_4$ | | | | x | x | | x |
| 9 | $Na_2O$, NaOH, $Na_2O_2$ | x | | | | | | |
|   | $MgSO_4$ | x | | x | x | x | | |
|   | $CaSO_4$ | | x | x | | | | |
| 10 | $Na_2O$, NaOH, $Na_2O_2$ | x | | | | | | |
|   | $MgSO_4$ | x | | x | x | x | | |
|   | $CaSO_4$ | | x | | | x | | |
|   | MAP/DAP | | | | x | | x | |
| 11 | $Na_2O$, NaOH, $Na_2O_2$ | x | | | | | | |
|   | $MgSO_4$ | x | | x | x | x | | |
|   | $CaSO_4$ | | x | | | x | | |
|   | MAP/DAP | | | | x | | x | |
|   | $FeSO_4$ | | | | x | x | | x |

In the above formulations, each formulation is preferably used to treat a substrate along with an oxidant; the alkaline agent preferably produces a hydroxide concentration of about $1\times10^{-4}$ M or greater; and each formulation preferably produces a soluble carbonate concentration that is lower than the soluble hydroxide concentration In the above formulations, CaO, $Ca(OH)_2$, and $CaO_2$ can be added in any combination and can be added or substituted with any combination of barium and strontium oxides, hydroxides, and peroxides. $CaSO_4$ can be added or substituted with any calcium salt. $Na_2O$, NaOH, $Na_2O_2$ can be added in any combination and can be added or substituted with any combination of Group 1 metal oxides, hydroxides, and peroxides. MgO, $Mg(OH)_2$, $MgO_2$ can be added in any combination and can be added or substituted with any combination of manganese oxides, hydroxides, peroxides, and permanganates. MAP/DAP can be added or substituted with any phosphate or nitrogen source. $FeSO_4$ can be added with or substituted with any iron salt, iron oxide, iron hydroxide, or zero valent iron.

In Formulations 1-11, the $HCO_3^-/CO_3^{-2}$ precipitation agent is added in an amount to ensure that it is not limiting for $HCO_3^-/CO_3^{-2}$ precipitation.

In Formulations 2-11, sulfate from persulfate, $CaSO_4$, $FeSO_4$, or any other separately added sulfate salt serves as an electron acceptor for bacteria if the system goes anaerobic. Sulfide derived from conversion of sulfate to sulfide will stabilize metals as metal sufides.

In Formulations 3 and 5 (or others), the $Na_2O$, NaOH, and $Na_2O_2$ can be added separately from $CaSO_4$ to form $Ca(OH)_2$ in situ. This makes field application easier than adding a slurry of $Ca(OH)_2$ directly.

In Formulations 9-11, the $Na_2O$, NaOH, and $Na_2O_2$ can be added separately from $MgSO_4$ to form $Mg(OH)_2$ in situ. This makes field application easier than adding a slurry of $Mg(OH)_2$ directly.

In Formulations 6-11, $Mg(OH)_2$ (either added directly or formed in situ) is less soluble than $MgCO_3$. A calcium, strontium, or barium salt is therefore added to form calcium, strontium, or barium carbonates or calcium magnesium carbonate ($CaMg(CO_3)_2$) in situ to lower the $CO_3^{2-}$ concentration. $Mg(OH)_2$ will stabilize amphoteric metals as metal hydroxides in an oxidized environment.

In Formulations 7, 8, 10, and 11, phosphates stabilize metals in an oxidized environment and serve as essential nutrients for biological activity. Depending on the formulation of the salt, nitrogen can be a cation (as in MAP and DAP) that serves as an additional essential nutrient for biological growth.

In Formulations 4, 5, 8 and 11, the iron salt can be added as a metal stabilizer or electron acceptor, depending on the iron salt, and as a catalyst for the oxidant.

In some versions, the formulations exclude calcium hydroxide, and the treatments exclude adding calcium hydroxide.

In some versions, the formulations exclude calcium hydroxide, potassium hydroxide, and/or sodium hydroxide, and the treatments exclude adding calcium hydroxide, potassium hydroxide, and/or sodium hydroxide.

The treatments described herein may include heating, such as to a temperature of at least about 40° C., about 50° C., about 60° C., about 70° C., about 80° C., about 90° C., or greater and/or up to about 99° C. or greater.

The reagents or formulations of the invention can be applied to the substrate in situ (e.g., an environmental site) or ex situ (e.g., a sample removed from an environmental site and placed in piles or tanks, etc.). The reagents or formulations of the invention can be applied by injection (gravity feed and/or pumping), continuous application, spraying, physical mixing, pump and pull, recirculation, permeable reactive barrier (PRB), and batch treatment, and any combination thereof, among others. The reagents or formulations of the invention can be applied as a solid form, a dissolved form, a slurry, or any combination thereof.

The oxides, hydroxides, peroxides or salts described herein encompass any hydrate forms thereof, whether explicitly stated or not.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the context clearly dictates otherwise.

The term "or" is used herein in the inclusive sense unless the context clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Background

Persulfate ion, hydrogen peroxide, percarbonate ion, and ozone, are exemplary oxidants that can be used in the present invention. The aforementioned oxidants are strong oxidizers by themselves, but the radicals they form have much higher oxidation potential, which thermodynamically favors oxidation and mineralization of organic compounds. Depending on the oxidant, activator/catalyst, and pH, varying radicals can form. Below are various activators and conditions that activate the above oxidants to form free radicals. Initiating, propagation, and terminating reactions are shown.

Persulfate

Iron: Fe(II) (Kolthoff et al. 1951):

$$2Fe^{+2}+S_2O_8^{-2} \rightarrow 2Fe^{+3}+SO_4\cdot+2SO_4^{-2} \quad \text{(eq. 1)}$$

Iron: Chelated Fe (Fe-EDTA):

$$S_2O_8^{-2}+Fe^{+2}-EDTA \rightarrow SO_4\cdot+SO4^{-2}+Fe^{+3}-EDTA \quad \text{(eq. 2)}$$

Alkaline:

$$S_2O_8^{-2}+H_2O+OH^- \rightarrow H_2O_2+2SO_4^{-2}+2H^+ \quad \text{(eq. 3)}$$

$$H_2O_2 \leftrightarrow HO_2^-+H^+ \quad \text{(eq. 4)}$$

$$HO_2^-+S_2O_8^{-2} \rightarrow SO_4\cdot+SO_4^{-2}+O_2\cdot+H^+ \quad \text{(eq. 5)}$$

$$SO_4\cdot+OH^- \leftrightarrow OH\cdot+SO_4^{-2} \quad \text{(eq. 6)}$$

Peroxide:

$$S_2O_8^{-2}+H_2O_2 \rightarrow SO_4\cdot+SO_4^{-2}+OH\cdot+OH^-$$

$$S_2O_8^{-2}+OH\cdot \rightarrow SO_4^{-2}+SO_4\cdot+\tfrac{1}{2}O_2+H^+ \quad \text{(eq. 7)}$$

Heat (House 1962):

$$S_2O_8^{-2}+\text{heat} \rightarrow SO_4\cdot \quad \text{(eq. 8)}$$

UV (Neta et al. 1977):

$$S_2O_8^{-2}+e^- \rightarrow SO_4\cdot+SO_4^{-2} \quad \text{(eq. 9.)}$$

Hydrogen Peroxide $$H_2O_2 \leftrightarrow HO_2^-+H^+ \quad \text{(eq. 10)}$$

Ozone $$O_3+OH^- \rightarrow \text{Reactive oxygen species (Staehelin et al. 1982)} \quad \text{(eq. 11)}$$

Percarbonate $$2Na_2CO_3\cdot 3H_2O_2 \rightarrow 2Na_2CO_3+3H_2O_2 \quad \text{(Eq. 12)}$$

The reactions above show a general pathway for oxidants to proceed. Various propagation reactions can form different radicals depending on the oxidant, pH, catalyst, substrate, and the decomposition products of the organic compounds oxidized. Radicals that form with the above technologies include hydroxyl radical (OH·), sulfate radical ($SO_4\cdot$), oxide radical (O·⁻), superoxide radical ($O_2\cdot$), perhydroxyl radical ($HO_2\cdot$), hydrogen trioxide radical ($HO_3\cdot$), and hydrogen tetraoxide radical ($HO_4\cdot$). Hydroxyl radicals were found to be the dominant radical produced with thermally activated persulfate at pH 11 (Liang and Huang 2012). The likely pathway is shown in eqs. 3-6. In alkaline conditions, ozone has been shown to produce a number of free radicals through of series of propagation reactions (Staehelin and Hoigné 1982). Equation 11 shows the initiating reaction. A series of propagation reactions occur that are not outlined herein but produce radicals including superoxide anion, perhydroxyl anion, hydroxyl, hydrogen tetraoxide, and hydrogen trioxide. At alkaline conditions, hydrogen peroxide is known to degrade faster than at neutral conditions. Fast hydrogen peroxide degradation can be detrimental in environmental remediation since the peroxide may not have enough time to contact the contaminants of concern before the peroxide is spent. Magnesium slows the degradation rate of hydrogen peroxide, which can be beneficial in environmental remediation (Lee et al. 2000).

Table 2 shows the oxidant and oxidation potential of free radicals, with the hydroxyl radical (OH.) having the highest potential and greatest ability to mineralize recalcitrant compounds.

TABLE 2

Oxidation Potential of Various Oxidants and Radicals

| Oxidant | Potential (V) | Source |
|---|---|---|
| Hydroxyl Radical (OH•) | 2.59 | Bossmann et al. 1998 |
| Sulfate Radical ($SO_4$•) | 2.43 | Huie et al. 1991 |
| Ozone ($O_3$) | 2.07 | Lide 2006 |
| Persulfate ($S_2O_8^{-2}$) | 2.01 | House 1962 |
| Hydrogen Peroxide ($H_2O_2$) | 1.776 | Lide 2006 |
| Carbonate Radical pH = 12 ($CO_3$•) | 1.59 | Huie et al. 1991 |

Bicarbonate and carbonate scavenge various free radicals, thereby inhibiting the oxidation process. Bicarbonate and carbonate can terminate the hydroxyl and sulfate radical reactions, for example, in the manner shown below.

Hydroxyl Radical Scavenging $$OH. + CO_3^{-2} \rightarrow OH^- + CO_3. \text{ (Buxton et al., 1988)} \quad (eq. 13)$$

$$OH. + HCO_3^- \rightarrow OH^- + HCO_3. \quad (eq. 14)$$

Sulfate Radical Scavenging $$SO_4. + CO_3^{-2} \rightarrow SO_4^{-2} + CO_3. \text{ (Zuo et al., 1999)} \quad (eq. 15)$$

$$SO_4. + HCO_3^- \rightarrow SO_4^{-2} + HCO_3. \quad (eq. 16)$$

In the presence of bicarbonate and carbonate, the hydroxyl radicals and sulfate radicals are converted to carbonate radicals (eqs. 13-16). Bicarbonate and carbonate radical scavenging may not be limited to hydroxyl and sulfate radicals. Other radicals, as outlined above, play an important role in propagation reactions that lead to the formation of hydroxyl and sulfate radicals. These intermediate radicals may be scavenged by bicarbonate and carbonate radicals, effectively terminating the reaction prior to hydroxyl and sulfate radical formation. The reaction rate of carbonate and the hydroxyl radical is 45 times faster than bicarbonate and hydroxyl radical (Buxton et. al., 1988). Therefore, the impact of carbonate scavenging increases as pH increases and bicarbonate shifts to carbonate.

In some cases, contaminant degradation stops in the presence of bicarbonate and carbonate, regardless of the amount of oxidant added or longevity of treatment. In alkaline activating applications, the ceasing of contaminant degradation may in part be due to converting hydroxide alkalinity to carbonate alkalinity (eqs. 17 and 18), thereby reducing soluble hydroxide concentrations and increasing soluble carbonate concentrations while still maintaining a pH>10. These conditions favor carbonate radical formation and terminate hydroxyl radicals (eqs. 13 and 14) and sulfate radicals (eqs. 15 and 16).

Precipitating carbonate ion minimizes the impact of carbonate radical scavenging. The form of carbon present is dependent on the pH of the system. When an alkaline agent is added and the pH is increased to greater than 10, inorganic carbon shifts from carbonic acid to bicarbonate to carbonate ion (eqs. 17 and 18). Therefore, under conditions of the invention, the carbonate ion ($CO_3^{-2}$) will predominate (eq. 18).

$$CO_2 + OH^- \leftrightarrow HCO_3^- + H^+ \text{ pH}=8.3 \quad (eq. 17)$$

$$HCO_3^- + OH^- \leftrightarrow CO_3^{-2} + H_2O \text{ pH}>10 \quad (eq. 18)$$

Available carbonate reacts with various metals to form insoluble metal carbonates. These metals may come from the substrate being oxidized but are preferably from added metal salts.

At a pH of greater than 10, alkalinity may be primarily in the form of $CO_3^{-2}$ rather than $OH^-$ (eq. 18). Thus, the particular alkaline agent used for radical formation is critical and simply maintaining a pH of greater than 10 is not the most effective way to generate radicals conducive to degrading recalcitrant organic contaminants.

Similarly, pH alone is not the best indicator of conditions suitable for alkaline activation. At a pH of greater than 10, $OH^-$ and $CO_3^{-2}$ ions exist, and $CO_3^{-2}$ ions may predominate. In some cases, the concentration of hydroxide is very low and the majority of the pH is due to the presence of carbonate ion (eq. 18). Higher carbonates will favor carbonate radicals (eqs. 13 and 15) rather than hydroxyl radical or sulfate radicals (eqs. 5-11). Rather than pH, hydroxide concentration and carbonate concentrations are better measures of effective alkaline activation. Therefore, speciation of the alkalinity is critical for radical formation.

At a pH of 10, and assuming no soluble carbonates, the hydroxide concentration would be $1 \times 10^{-4}$ M. The higher the hydroxide concentration the more likely the reaction will favor an alkaline pathway radical formation. A dissolved hydroxide concentration greater than a dissolved carbonate concentration favors hydroxide and sulfate radicals and minimizes carbonate radical scavenging (eqs. 13 and 15).

$OH^-$ ions and $CO_3^{-2}$ ions can react with metals to form insoluble metal hydroxides or insoluble metal carbonates. Most metal hydroxides are more insoluble than their respective metal carbonate. Therefore, in the presence of both available $OH^-$ and $CO_3^{-2}$, metal hydroxides under many conditions will precipitate first until all of the available $OH^-$ has reacted or until the metal hydroxide has reached its solubility product. This produces dissolved $[OH^-]$<dissolved $[CO_3^{-2}]$. Metal carbonate will form once the solubility concentration of the metal hydroxide is achieved and there are available metal ions to react with the carbonate.

Calcium is a metal where its carbonate is more insoluble than its hydroxide. Calcium forms more insoluble calcium carbonate ($K_{sp}=5.0 \times 10^{-9}$) than calcium hydroxide ($K_{sp}=4.7 \times 10^{-6}$). Adding a soluble or slightly soluble calcium salt to a pH of greater than 10 in the presence of available $CO_3^{-2}$ ions and $OH^-$ ions, the following reactions occur.

$$CO_3^{-2} + OH^- + Ca^{+2} \rightarrow CaCO_3\downarrow + OH^- \ CO_3^{-2} \text{ precipitates first} \quad (eq. 19)$$

$$CO_3^{-2} + OH^- + Ca^{+2} \rightarrow CaCO_3\downarrow + Ca(OH)_2\downarrow \text{ After } CO_3^{-2} \text{ precipitates} \quad (eq. 20)$$

Because calcium carbonate is more insoluble than calcium hydroxide, calcium carbonate will precipitate before calcium hydroxide. Based on a calcium hydroxide $K_{sp}$ of $4.7 \times 10^{-6}$, a pH of 12.32 and a soluble hydroxide concentration of $2.11\times10^{-2}$ M will be achieved at equilibrium. At the same pH, the dissolved carbonate concentration would be $7.00\times10^{-5}$ M using a calcium carbonate $K_{sp}$ of $5.0\times10^{-9}$. The dissolved $[OH^-]\gg$dissolved $[CO_3^{-2}]$, thus effectively sequestering $CO_3^{-2}$ ions that can scavenge radicals and providing ample hydroxyl ions for free radical formation (eqs. 19 and 20).

Calcium is the limiting reagent for the formation of calcium carbonate and should be available in a form that is equal to or greater than the carbonate concentration for effective carbonate sequestration. In some environmental systems, lime $(Ca(OH)_2)$ can be used alone as a source of hydroxide and calcium ions but provides insufficient calcium ions under most systems. Most environmental systems have a pH near neutral, wherein bicarbonate is the predominant carbon species. pH adjustment of bicarbonate to carbonate ion by lime is shown in equation 21.

$$2HCO_3^- + Ca(OH)_2 \leftrightarrow CaCO_3 + CO_3^{-2} + 2H_2O \quad \text{(eq. 21)}$$

Under these conditions, 2 moles of $CO_3^{-2}$ ions to one mole of $Ca^{+2}$ ions will be produced, thereby sequestering only one $CO_3^{-2}$ ion. Increasing the lime dosage to meet the calcium requirement of a system will result in a higher hydroxide concentration than needed for alkaline activation. For example, 2 moles of $OH^-$ will be released for every mole of $Ca^{+2}$. Too high of a hydroxide concentration leads to mobilization of amphoteric metals, causing a secondary contaminant problem. Calcium also reacts with other metals or ions in the system and form insoluble calcium compounds. Co-precipitation with other metals and precipitation with ions, such as phosphate, will reduce the soluble calcium concentration and limit the effectiveness of carbonate sequestering. During oxidation, organic carbon will be oxidized to inorganic carbon and be converted to carbonate. By adding a slightly soluble or soluble calcium salt, the calcium concentration can be maintained in excess of the carbonate concentration without increasing hydroxide concentrations to levels that mobilize amphoteric metals.

Suitable alkaline agents for use in the present invention include metal hydroxides, oxides, and peroxides that produce soluble hydroxide concentrations near $1\times10^{-4}$ M or greater at equilibrium and have a corresponding metal carbonate $K_{sp}$ that is lower than the respective metal hydroxide $K_{sp}$ (i.e., the metal carbonate $K_{sp}$ is less soluble than the respective metal hydroxide). Such alkaline agents include Group 2 metal oxides, hydroxides, and peroxides, such as hydroxides, oxides, and peroxides of calcium, strontium, and barium.

Oxides, hydroxides, and peroxides of Group 1 metals are also suitable alkaline agents given a soluble or slightly soluble Group 2 metal salt is added in the stoichiometric amount required to convert the Group 1 alkaline agent to a Group 2 alkaline agent. For example, sodium hydroxide can react with a slightly soluble or soluble calcium salt such as calcium sulfate to form calcium hydroxide when the calcium salt is added at the stoichiometric amount of sodium hydroxide. When the calcium salt is added in excess of the stoichiometric amount of sodium hydroxide, excess calcium ions will be available to sequester carbonates (eq. 22).

$$2NaOH + Ca^{+2}\text{-Salt}_{(in\ excess)} \leftrightarrow Ca(OH)_2 + Na_2\text{-Salt} + Ca\text{-Salt} \quad \text{(eq. 22)}$$

Forming calcium hydroxide with a soluble Group 1 oxide, hydroxide, or peroxide metal and a calcium salt is beneficial when applying the chemistry through injection wells or direct push probes, such as an In-situ Chemical Oxidation (ISCO). Because calcium hydroxide is only slightly soluble, it will form a slurry with injection water used in an ISCO application. The slurry can be difficult to inject and can fill the pore spaces near the injection point, thereby limiting chemical influence in the subsurface. Calcium hydroxide will also form a slurry in the supply tank, requiring specialized equipment to inject the chemical. By adding a soluble calcium salt and sodium hydroxide separately, all the chemicals will be dissolved during application and calcium hydroxide will form in situ. This process eliminates injecting a slurry, allows for greater radius of influence around the injection point, and eliminates the need for specialized equipment.

Other suitable alkaline agents include metal hydroxides, oxides, and peroxides that produce hydroxide concentrations near $1\times10^{-4}$ M or greater but have corresponding metal carbonates that are more soluble than their respective metal hydroxides, provided an additional metal salt that forms insoluble carbonates is added. For example, if a magnesium salt is added to a solution with a pH of greater than 10 in the presence of both soluble hydroxide and soluble carbonate ions and the magnesium concentration is equal to the stoichiometric amount of $OH^-$, then magnesium hydroxide would be the predominant form of magnesium (eq. 23). A magnesium hydroxide $K_{sp}$ of $5.6\times10^{-12}$ will produce a hydroxide concentration of $2.24\times10^{-4}$ M at equilibrium (pH=10.35), meeting the hydroxide concentration criterion of $1\times10^{-4}$ M. At a pH of 10.35 and a magnesium carbonate $K_{sp}$ of $6.8\times10^{-6}$, a carbonate concentration of $1.34\times10^{-3}$ M is found assuming all carbon is as carbonate. If magnesium is added in excess of the stoichiometric amount of $OH^-$ for forming magnesium hydroxide, magnesium hydroxide will precipitate first (eq. 23) followed by magnesium carbonate (eq. 24).

$$CO_3^{-2} + OH^- + Mg^{+2} \rightarrow Mg(OH)_2\downarrow + CO_3^{-2}\ OH^-\ \text{precipitates first} \quad \text{(eq. 23)}$$

$$CO_3^{-2} + OH^- + Mg^{+2} \rightarrow Mg(OH)_2\downarrow + MgCO_3\downarrow\ \text{After } OH^-\ \text{precipitates} \quad \text{(eq. 24)}$$

$$CO_3^{-2} + OH^- + Mg^{+2} + Ca^{+2} \rightarrow Mg(OH)_2\downarrow + CaCO_3\downarrow + Mg^{+2}\ \text{After } OH^-\ \text{precipitates} \quad \text{(eq. 25)}$$

Given the above reaction, magnesium hydroxide will preferentially precipitate over magnesium carbonate. In this example, the dissolved hydroxide concentration of $2.24\times10^{-4}$ M is less than the dissolved carbonate concentration of $1.34\times10^{-3}$ M; dissolved $[OH]<$dissolved $[CO_3^{-2}]$. Subsequently, higher dissolved concentrations of carbonates than dissolved hydroxides will favor radical scavenging by carbonates (eqs. 13 and 15). The dissolved carbonate concentration is dependent on the solubility of the metal carbonate. Carbonates will precipitate assuming other metal salts that form more insoluble metal carbonates than magnesium carbonate and produce a metal hydroxide concentration near $1\times10^{-4}$ M or greater at equilibrium are added. For example, if a calcium salt is also included in the above mixture, calcium carbonate $(K_{sp}=5.0\times10^{-9})$ will precipitate before magnesium carbonate $(K_{sp}=6.8\times10^{-6})$, thereby effectively sequestering $CO_3^{-2}$ ions that scavenge radicals (eq. 25). In this condition, dissolved $[OH]>$dissolved $[CO_3^{-2}]$.

U.S. Pat. No. 7,575,254 to Block et al. identifies sodium hydroxide, potassium hydroxide, and calcium hydroxide as pH modifiers for persulfate, where the modifier is added to achieve a pH near 10 or greater. The preferred modifier is sodium hydroxide (NaOH) (PeroxyChem. Activating Klozur® SP with a 25% Sodium Hydroxide Solution). At the prescribed pH, alkalinity will exist as both hydroxide ion and carbonate ion. The method of Block et al., however, does not take into consideration pretreatment carbonate concentrations or the formation of carbonate as chemical oxidation degrades organic compounds to inorganic carbon. Of particular importance is the mineralization of organic compounds to inorganic carbon ($CO_2$) as oxidation proceeds. The building of inorganic carbon in the system will utilize hydroxide ion (eqs. 17 and 18) and convert hydroxide alkalinity to carbonate alkalinity under conditions described therein. Therefore, as oxidation proceeds, the hydroxide concentration will decrease and the carbonate concertation will increase. As stated above, carbonate ion will scavenge hydroxyl and sulfate radicals and form carbonate radicals, which are inefficient in chemical oxidation. In the method of Block et al., it is possible that all of the alkalinity exists as carbonate ion and very little, if any, of the alkalinity exists as hydroxide ion. In all carbonate systems, a pH of greater than 10 is possible, thereby meeting the pH criteria prescribed by Block et al., but little, if any, hydroxide ion will exist. Therefore, the reaction pathways shown in equations 3-6 will not be favored since hydroxide ion is required in the propagation reactions. Instead, carbonate radical scavenging will be favored (eqs. 5-8) due to the high carbonate alkalinity.

An aspect of the invention is controlling mobilization of metals, such as amphoteric metals, at high pH. Amphoteric metals are metals that are soluble at both high and low pH levels. Examples of amphoteric metals include aluminum, chromium, gallium, copper, antimony, lead, bismuth, indium, silicon, titanium, vanadium, iron, cobalt, germanium, zirconium, zinc, silver, tin, and gold. Reactions showing the mobilization of amphoteric metals at both acidic and basic conditions are shown below.

$$\text{Acid: } ZnO+2H^+ \rightarrow Zn^{+2}+H_2O \qquad (\text{eq. 26})$$

$$\text{Base: } ZnO+H_2O+2OH^- \rightarrow Zn(OH)_{4\ (aq)}^{-2} \qquad (\text{eq. 27})$$

$$\text{Acid: } Al_2O_3+3H_2O+6H^+ \rightarrow 2Al(H_2O)_6 \qquad (\text{eq. 28})$$

$$\text{Base: } Al_2O_3+3H_2O+2OH^- \rightarrow 2Al(OH)_{4(aq)} \qquad (\text{eq. 29})$$

$$\text{Acid: } PbO+2H^+ \rightarrow Pb^{+2}+H_2O \qquad (\text{eq. 30})$$

$$\text{Base: } PbO+H_2O+2OH^- \rightarrow Pb(OH)_{4\ (aq)}^{-2} \qquad (\text{eq. 31})$$

Elevated levels of dissolved amphoteric metals are observed after oxidant treatment, such as alkaline-activated persulfate treatment (Wenzel 2012, Osgerby 2011, Krembs 2008). There are pathways for the natural attenuation of the metals. For example, dissolved amphoteric metal concentrations decrease over time as elevated pH is neutralized by soil and groundwater outside of the treatment zone and when the decomposition of persulfate forms sulfuric acid which can neutralize the alkalinity (Wenzel, 2012). These pathways, however, may take months to years to be achieved. In low permeable soils, the groundwater flow may be so low that it may take years to infiltrate non-treated soils. The amount of alkaline agent added can also influence the attenuation of the metals. If the alkaline agent is added in excess of the stoichiometric formation of sulfuric acid during persulfate decomposition, the pH will remain high after all of the persulfate is utilized and subsequently result in high dissolved amphoteric metals concentrations, thereby requiring a longer time period for the substrate to neutralize the excess alkalinity.

Magnesium oxide, magnesium hydroxide, and magnesium peroxide have a pH of 10.35 in water at saturation ($K_{sp}$=5.61×10$^{-12}$). While sodium hydroxide, potassium hydroxide, calcium oxide, calcium hydroxide, and calcium peroxide have a pH of greater than 12 at saturation. The higher the pH, the greater the solubility of amphoteric metals. The result is an increase in dissolved amphoteric metals in groundwater in areas influenced by alkaline persulfate treatment. Leachability of the wastes treated with sodium hydroxide, potassium hydroxide, calcium oxide, calcium hydroxide, and calcium peroxide will also result in an increase in dissolved amphoteric metals.

Metal mobilization can be controlled by alkaline-activating the oxidant with magnesium hydroxide. Magnesium oxide is less soluble than other alkaline agents (CaO, NaOH), so the concentration of soluble hydroxide is less than other alkaline agents but still has enough total alkalinity to neutralize acids while not increasing the pH to a level where amphoteric metals dissolve.

Sodium hydroxide and potassium hydroxide are very soluble in water. Therefore, increasing the pH to greater than 10 may not require much chemical, as it will completely dissociate when added to water and increase the pH quickly with lower molar masses. Calcium hydroxide is less soluble in water ($K_{sp}$=4.7×10$^{-6}$) and may require a higher molar concentration to achieve the same pH. Magnesium oxide, hydroxide, and peroxide are even less soluble in water ($K_{sp}$=5.6×10$^{-12}$). Magnesium oxide, hydroxide, and peroxide will therefore require higher molar concentrations to achieve a similar pH due to this lower solubility. In fact, the highest attainable pH with magnesium oxide, hydroxide, and peroxide is roughly 10.3. Although the pH is lower, the total alkalinity added can equal the total alkalinity of sodium hydroxide. This is particularly important alkaline activation of oxidant, as total alkalinity, not merely pH, is the appropriate indicator for effective alkaline activation.

Sodium hydroxide is conventionally added for persulfate activation to compensate for two factors: (1) The amount of sodium hydroxide needed to overcome natural acidity in the material treated and achieve a pH of greater than 10; and (2) The amount of sodium hydroxide needed to compensate for the formation of sulfuric acid when persulfate decomposes (e.g., PeroxyChem. Activating Klozur® SP with a 25% Sodium Hydroxide Solution). Depending on the persulfate dosage, and assuming total utilization of persulfate, the amount of sodium hydroxide required for persulfate decomposition can be two or three times higher than that required for overcoming the natural acidity. When applied, the initial total alkalinity required well exceeds the amount needed to achieve a pH of greater than 10. Laboratory testing has shown pH levels of greater than 12.5 after initial persulfate dosages. At these pH levels, amphoteric metals will increase in solubility. By contrast, activation with magnesium oxide, hydroxide, or peroxide, regardless of dosage, will achieve a pH of roughly 10.35. Dosages of magnesium oxide, hydroxide, or peroxide that meet the natural acidity and decomposition of persulfate will not see a spike in pH after initial application, therefore lowering amphoteric metal solubility while still maintaining an alkalinity concentration that is effective for alkaline activating persulfate and neutralizing all the sulfuric acid from the decomposition of persulfate.

The lower pH resulting from magnesium oxide, hydroxide, or peroxide is also less detrimental on degrader microbe populations, which aids in the decontamination process.

Any metals dissolved in the substrate can be sequestered with a metal stabilization agent. Suitable stabilization agents include sulfates, sulfides, phosphates, iron, and silicates. In the case of sulfates, phosphates, and silicates are anions and can be added as a counterion for calcium, magnesium, and iron (preferably reduced iron). Sulfates can also be introduced in situ with the use of persulfate as an oxidant. The persulfate ion, for example, will produce sulfate as a product. After oxidation, some systems may move from and aerobic/oxidized environment to an anaerobic/reduced environment through biological activity. Microbial degraders that break down organic contaminants can use the sulfate ion as an electron acceptor and convert sulfate to sulfide ion. The sulfide ion can complex with metals to form metal sulfides, which are very insoluble. Iron, such as that provided in the form of reduced iron salt, can also be used as an electron acceptor by microbes and sequester metals in a similar manner. Phosphates combine with metals to form metal phosphates, which are very insoluble and precipitate out of solution. In addition to phosphates acting as a stabilizing agent, they are also a nutrient for microbes involved in degradation. Nitrogen can also provide essential nutrients to stimulate biological conditions. Nitrogen can be added directly or as a nitrogen salt, such as a salt of a metal stabilizer or precipitating agent.

Thus, in some versions of the invention, metals are stabilized in oxidative/aerobic environments by using magnesium hydroxide and a metals stabilizer and in reductive/anaerobic environments by forming metal sulfides.

Sequestering carbon as a metal carbonate and bicarbonate prior to a system biologically converting to anaerobic conditions has the benefit of reducing available carbon sources that can be converted to methane. Reducing available carbon for methane production has the following benefits:

1. Reduces intrusion of methane into dwellings where concentrations can increase to unsafe levels, requiring additional engineering practices to mitigate methane intrusion.
2. Reduces methane production which is a major greenhouse gas.
3. Reduces methylation of metals such as mercury. Methylmercury is more biologically available and biomagnifies in the environment.

Experimental Demonstration 1

Methylene Blue (MB) was found to be an effective chemical probe for the evaluation of persulfate and peroxide chemistries. Upon oxidation of MB by hydroxyl radicals, the MB goes from dark blue to colorless (Satoh et al. 2007). Sulfate radicals were also found to oxidize MB from dark blue to colorless (Liang et al. 2012). However, hydrogen peroxide alone does not oxidize MB (Satoh et al. 2007) and persulfate ion alone does not oxidize MB (Liang et al. 2012). Therefore, MB is an effective chemical probe to evaluate free radical chemistries. The dark blue color from the MB is quantified by UV-Vis.

Kinetic experiments measured the rate of oxidation of MB by persulfate under alkaline conditions (pH greater than 10). Kinetic experiments were designed to measure reaction rates with $OH^-$ as a sole alkaline agent in the manner of U.S. Pat. No. 7,576,254 to Block et al., $OH^-$ and $CO_3^{-2}$ as alkaline agents, $OH^-$ and $CO_3^{-2}$ as alkaline agents in combination with a calcium salt, and $CO_3^{-2}$ as a sole alkaline agent. See FIG. 1.

In the experimental design, the initial sodium persulfate (SPS) concentration was $7.37 \times 10^{-3}$ M, and the initial MB concentration was $1.61 \times 10^{-5}$ M for all tests. It can be assumed that the [SPS] is >>[MB] (~458 times greater SPS than MB) and, under these experimental conditions, the degradation rate of MB can be expressed by a pseudo-first order reaction:

$$\frac{-dC_{MB}}{dt} = K_{obs,CM} C_{CM}$$

where $K_{obs,CM}$ is the observed pseudo-first order rate constant for the degradation of MB.

Alkaline activation of SPS with the addition of sodium hydroxide (NaOH) to a pH greater than 10 is consistent with a method as presented by Block et al. (U.S. Pat. No. 7,576,254). Kinetic testing was performed by measuring the degradation rate of MB following similar procedures described by Liang et al. 2012. The SPS solution was activated with hydroxide, as NaOH, at $1.74 \times 10^{-2}$ M. The [$OH^-$] concentration reflects the concentration required to obtain a pH of 11.0 and to account for the formation of sulfuric acid from the degradation of SPS to sulfuric acid. The $OH^-$ addition assumes all of the SPS degrades and forms sulfuric acid. For experiments where free carbonates were added, a carbonate concentration of $1.98 \times 10^{-2}$ M $CO_3^{-2}$ as sodium carbonate was used. Experiments where a calcium salt was added, calcium sulfate dihydrate ($CaSO_4 + 2H_2O$) was added at a concentration of $3.78 \times 10^{-2}$ M.

Testing was conducted in open 1000 ml beakers where the beaker was slightly agitated on a shaker table. Experiments were performed a 20° C.+/−1° C. in deionized water. 500 ml of test solution was prepared. A 10-ml aliquot of solution was collected at various times and measured for MB, SPS, hydroxide alkalinity, carbonate alkalinity, and pH. SPS was analyzed by methods similar to Haselow et al. 2003. MB testing was performed using procedures similar to Liang et al. 2012. Alkalinity was measured by potentiometrically titrating the sample to a pH of 8.3 and then to a pH of 4.3 with standardized sulfuric acid on an Orion 720A+ pH meter. The aliquot of solution was centrifuged/filtered through a 0.45 μm filter prior to analysis to remove any precipitates that would interfere with the analytical procedure.

Results are shown in FIG. 1 and Table 3.

TABLE 3

Test Conditions, Reaction Rates, pH, Hydroxide Concentration, and Carbonate Concentrations

| $OH^-$ [M] | $CO_3^{-2}$ [M] | $CaSO_4 \cdot 2H_2O$ [M] | $k_{obs} M^{-1} S^{-1}$ | $R^2$ | ½ life (min) | Overall Rate Constant $M^{-1} S^{-1}$ | pH Range (initial - final) | $OH^-$ [M] (initial - final) | $CO_3^{-2}$ [M] (initial - final) |
|---|---|---|---|---|---|---|---|---|---|
| 1.74E−03 | — | — | 5.67E+01 | 0.999 | 18.1 | 1.49E−08 | 12.67-12.46 | 1.42E−02-1.24E−02 | 1.47E−03-1.96E−03 |
| 1.74E−03 | 1.98E−02 | — | 4.77E+01 | 0.996 | 21.5 | 1.25E−08 | 12.69-12.44 | 1.12E−02-8.23E−03 | 1.94E−02-2.08E−02 |
| 1.74E−03 | 1.98E−02 | 3.78E−02 | 8.51E+01 | 0.995 | 12.1 | 2.24E−08 | 12.73-12.48 | 1.31E−02-1.03E−02 | 9.80E−05-8.82E−04 |
| — | 1.98E−02 | — | 1.40E+01 | 0.988 | 75.6 | 3.47E−09 | 11.51-11.60 | <Detection | 1.68E−02-1.84E−02 |

Note: For all Experiments, [SPS] = 7.37 × $10^{-3}$ M, [MB] = 1.61 × $10^{-5}$ M Residual SPS concentrations remained greater than 90% for all tests performed (data not shown), thereby, maintaining conditions for a pseudo-first order reaction.

An initial and final pH of >11 was achieved for all tests (Table 3). Therefore, carbonate ion is the predominant form of carbon. The initial and final pH ranges were consistent for all tests where hydroxide was added. The pH was lower, but still greater than 10, for the carbonate only test (Table 3). The carbonate only test shows all of the alkalinity is from carbonates and no measurable alkalinity is from hydroxide.

A slight increase in carbonates was observed during testing. The carbonate ion increase from the initial to final test time is attributed to atmospheric $CO_2$, which is converted to $CO_3^{-2}$ under the test conditions used (eqs. 17 and 18). The $OH^-$ only test, representing the method of Block et al., showed an increase in $CO_3^{-2}$ concertation during testing with none of the carbonate being sequestered. Conversion of $CO_2$ to $CO_3^{-2}$ also occurred in the conditions of the present invention ($OH^-$ and $CO_3^{-2}$+calcium salt), but the $CO_3^{-2}$ was sequestered as shown in eq. 19. In fact, the conditions of the invention removed greater than 95% of the spiked carbonate, whereas the other tests found no carbonate removal. This produced dissolved $[OH^-]$>>dissolved $[CO_3^{-2}]$, thus effectively sequestering $CO_3^{-2}$ ions that can scavenge radicals and providing ample hydroxyl ions for free radical formation (eqs. 19 and 20).

Reaction rates ($k_{obs}$) were calculated on data where MB was degraded by at least 75% (C/Co [MB]<0.25). A C/Co of <0.25 was not achieved for the $CO_3^{-2}$ only test, therefore data up to 80 minutes was used (FIG. 1). Reaction rates clearly show the negative impact of available $CO_3^{-2}$ on SPS oxidation of MB. The reaction rates from the fastest to the slowest were as follows: $OH^-$ and $CO_3^{-2}$+calcium salt (present invention)>$OH^-$ only (method of Block et al.)>$OH^-$ and $CO_3^{-2}$>>$CO_3^{-2}$ only (Table 3). Atmospheric contribution of $CO_2$ and conversion to $CO_3^{-2}$ was found to impact the reaction rate in the method of block et al. The data show that $CO_3^{-2}$ concentrations of $1.47\times10^{-3}$ M have a negative impact on MB degradation.

invention. The conditions of the present invention, with a $CO_3^{-2}$ spike of $1.98\times10^{-2}$ M and in the presence of available calcium, had a reaction rate that was approximately 1.5 times faster than the method of Block et al. A higher reaction rate with the conditions of the present invention was achieved even though the conditions of Block et al. did not include a $CO_3^{-2}$ spike. The conditions of the present invention removed available $CO_3^{-2}$ to a concentration of $9.80\times10^{-3}$ M. A higher $CO_3^-$ concentration was found in the $OH^-$ only test. An initial $CO_3^{-2}$ concentration in the conditions of Block et al. test was $1.47\times10^{-3}$ M, and a final concentration was $1.96\times10^{-3}$ M. At available $CO_3^{-2}$ concentrations of $-1.47\times10^{-3}$ M, the influence of $CO_3^{-2}$ was observed in the reaction rate.

This example shows available $CO_3^{-2}$ can be effectively sequestered with metal salts that form insoluble metal carbonates, thereby eliminating carbonate radical scavenging.

Experimental Demonstration 2

Further testing using magnesium oxide (MgO) as an alkaline agent for persulfate and MB as a chemical probe were conducted. Testing was performed to demonstrate other alkaline agents that have a metal carbonate solubility greater than their respective metal hydroxide solubility are effective alkaline agents. In this case, $MgCO_3$ has a greater solubility than $Mg(OH)_2$. Carbonate is sequestered in the present case by adding a salt of a metal that forms a metal carbonate with a lower solubility than any metal carbonate formed from the alkaline agent. For example, adding a calcium salt such as $CaSO_4.2H_2O$ precipitates carbonates as $CaCO_3$, thereby sequestering available carbonate.

Reagent concentrations were identical to testing shown in Table 3. To remove the effect of atmospheric $CO_2$ converting to $CO_3^{-2}$, testing was performed in vessels that were not exposed to the atmosphere. Dissolved calcium and magnesium were also analyzed.

Figure 2:
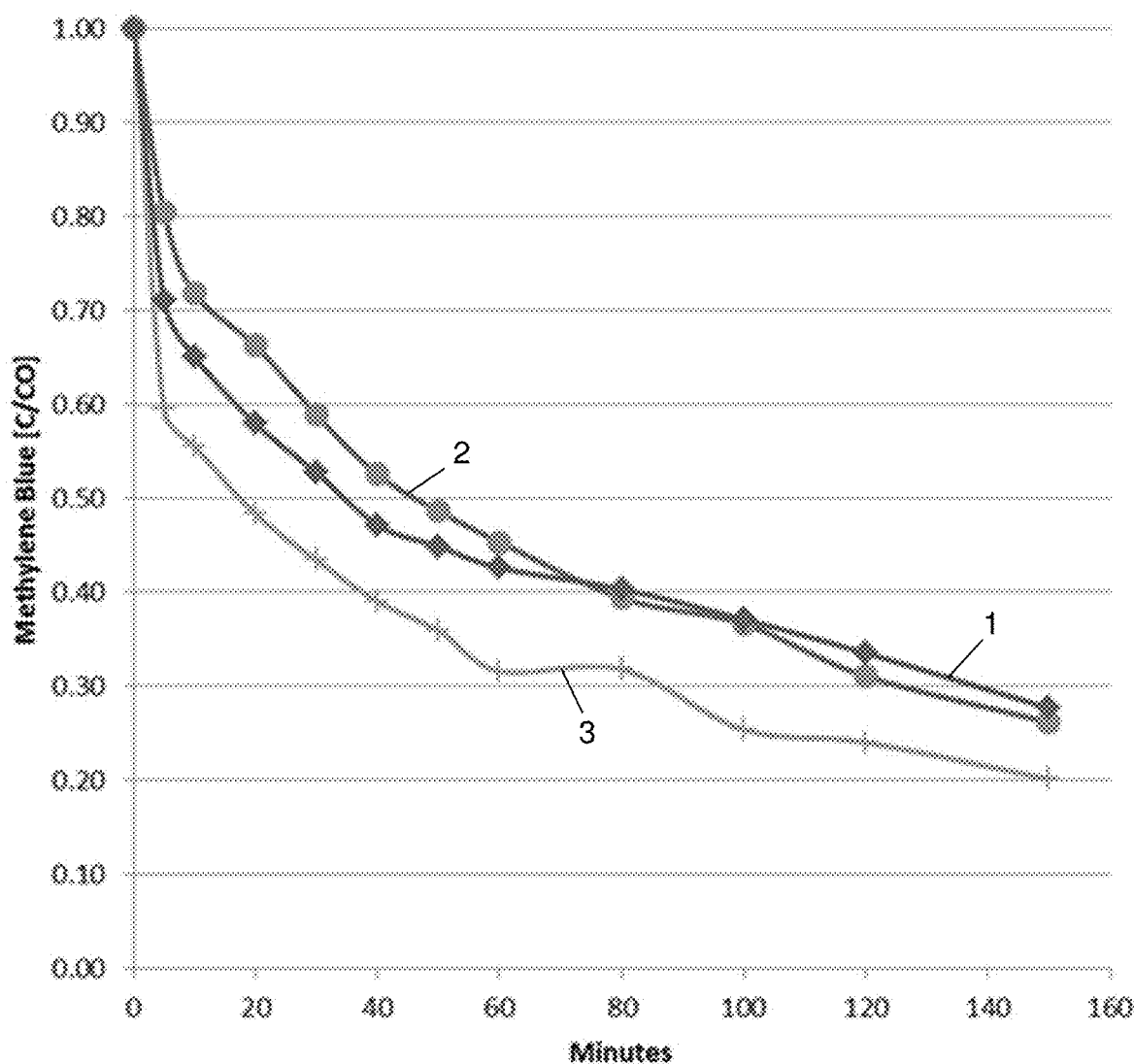
FIG. 2 shows degradation of methylene blue (MB) with varying alkaline activation conditions for oxidants.

Results are shown in FIG. 2 and Table 4.

TABLE 3

Test Conditions, Reaction Rates, pH, Hydroxide Concentration, and Carbonate Concentrations, Calcium Concentration, and Magnesium Concentration

| $OH^-$ [M] (1) | $CO_3^{-2}$ [M] | $CaSO_4 \cdot 2H_2O$ [M] | $k_{obs}M^{-1}S^{-1}$ | $R^2$ | ½ life (min) | Overall Rate Constant $M^{-1} S^{-1}$ | pH Range (initial - final) | Average [$OH^-$] | Average [$CO_3^{-2}$] | Average [$HCO_3^-$] | Average Ca, mg/L | Average Mg, mg/L |
|---|---|---|---|---|---|---|---|---|---|---|---|---|
| 1.74E−02 | — | — | 1.48E+01 | 0.978 | 67.9 | 4.06E−09 | 9.57-9.80 | 9.57E−05 | 2.89E−04 | 6.64E−04 | 3.39 | 13.7 |
| 1.74E−02 | 1.98E−02 | — | 1.75E+01 | 0.996 | 57.4 | 4.81E−09 | 11.01-10.55 | 6.49E−04 | 1.48E−02 | 5.21E−03 | 2.49 | 10.1 |
| 1.74E−02 | 1.98E−02 | 3.78E−02 | 2.60E+01 | 0.968 | 39.6 | 6.82E−09 | 8.74-10.00 | 1.11E−04 | 2.70E−04 | 5.94E−04 | 527 | 17.5 |

Note:
For all Experiments, [SPS] = $7.37 \times 10^{-3}$ M, [MB] = $1.61 \times 10^{-5}$ M. The total hydroxide added is $1.74 \times 10^{-2}$ M, but the amount of $OH^-$ soluble at any given time is limited by the solubility if $Mg(OH)_2$. Based on $Mg(OH)_2$ Ksp of $5.61 \times 10^{-12}$, the $OH^-$ M solubility is $2.24 \times 10^{-4}$.

The experiment with only available carbonate as the alkaline agent showed the slowest reaction rate ($K_{obs}$=$1.04\times10^1$, 75.6 min ½ life) (Table 3). Note also there was no detectable hydroxide to generate hydroxyl radicals. Therefore, carbonate ions and sulfate ions are the dominant ions in solution, and all of the alkalinity is from carbonate. Given these considerations, carbonate radicals are likely scavenging sulfate radicals (eqs. 15 and 16).

The reaction rate is dependent on the $CO_3^{-2}$ concentration. In the hydroxide alone experiment, which represents the method of Block et al., the reaction rate is slower than the reaction rate found under the conditions of the present Residual SPS concentrations remained greater than 99% for all tests performed (data not shown), thereby, maintain conditions for a pseudo-first order reaction.

An initial and final pH of ≈10 or greater was achieved for all tests (Table 4). At a pH near 10, both carbonate and bicarbonate will be present. Therefore, speciation of the carbonate was conducted. As noted in Table 4, the hydroxide concentration is controlled by solubility of $Mg(OH)_2$, which theoretically is $2.24\times10^{-4}$ M at saturation. The $OH^-$ only test and $OH^-$+$CO_3^{-2}$+calcium salt found pH levels and $OH^-$ below the theoretical values of 10.35 and $2.24\times10^{-4}$ M, respectively. Lower levels are likely due to neutralization by sulfuric acid from persulfate. A higher pH was observed in the OH$^-$+CO$_3^{-2}$ due to the presence of soluble carbonates (Table 4). Because CO$_3^{-2}$ was added as Na$_2$CO$_3$, which is completely soluble, soluble carbonates were available to neutralize sulfuric acid from the persulfate.

The OH$^-$+CO$_3^{-2}$ test shows none of the carbonates were sequestered (Table 4). Contrary to that test, the OH$^-$+CO$_3^{-2}$+calcium salt test found 96% of the spiked carbonate was sequestered—carbonate and bicarbonate concentrations were added together to get the total carbonate concentration. The data clearly show the addition of an alkaline magnesium agent or magnesium salt+other alkaline agent alone cannot sequester carbonates to levels that don't negatively impact the efficiencies of SPS. The addition of CaSO$_4$.2H$_2$O sequestered the carbonates and produced a residual dissolved calcium concentration that can further sequester inorganic and organic carbon from various sources, including organic contaminant mineralization, soil fractions, enhancement additives, among others. With the addition of a calcium salt, carbonates are sequestered and improved SPS effectiveness is observed. This is illustrated in the reaction rates.

Reaction rates ($k_{obs}$) were calculated on data where the MB degraded to at least 75% (C/Co [MB]<0.25) or the entire 150 minute test if a [MB]<0.25 was not achieved. The OH$^-$+CO$_3^{-2}$+calcium salt test was the only test to achieve [MB]<0.25 (FIG. 2). Reaction rates clearly show sequestering carbonates improve the efficiency of SPS. The reaction rates from fastest to slowest were as follows; OH$^-$+CO$_3^{-2}$+calcium salt (present invention)>OH$^-$+CO$_3^{-2}$>/≈OH$^-$ only (Table 4). The present invention found a reaction rate approximately 1.7 times faster than when Mg(OH)$_2$ alone was used.

This example, as well as the example where NaOH was the alkaline agent, shows sequestering carbonates eliminate carbonate radical scavenging and improve the efficiency of SPS. This example also demonstrates that alkaline magnesium agents alone will not lower soluble carbonate concentrations to levels that don't negatively influence the effectiveness of oxidants. Alkaline magnesium agents plus the addition of a metal salt (i.e., calcium salt) where the metal salt produces less soluble metal carbonates than metal hydroxides did show a significant improvement in oxidant effectiveness by sequestering carbonates and eliminating carbonate radical scavenging.

Experimental Demonstration 3

Metals mobilization of soil treated with SPS and activated by (1) NaOH, (2) Mg(OH)$_2$, (3) Mg(OH)$_2$+phosphate (TSP), and (3) in-situ formation of Mg(OH)$_2$ by adding stoichiometric amounts of NaOH+MgSO$_4$+7H$_2$O to produce Mg(OH)$_2$ were tested. Two test soils containing chlorinated volatile organic contaminates (CVOC) comprising trichloroethylene (TCE) and daughter products of TCE were tested. Soil acidity for each soil was measured and an appropriate amount of alkaline agent was used to bring the soil to a pH of approximately 10.5. An appropriate amount of alkalinity was also added to account for the formation of sulfuric acid from the SPS. Soil acidity and acidity from the SPS accounted for the total acidity. An appropriate amount of alkaline agent was used to neutralize the total acidity. Alkaline activation chemistries (NaOH, Mg(OH)$_2$, etc.) were added such that the hydroxide concentrations were equal.

For testing, a SPS dosage of 10 g SPS/kg soil was added with the appropriate amount of alkaline agent. The alkaline agent was added at the stoichiometric amount to neutralize the total acidity (1×) and at three times the stoichiometric amount (3×). Three times the stoichiometric amount was tested to illustrate metals mobilization if the total acidity is overestimated and excess alkalinity is added.

The persulfate Total Oxidant Demand (TOD) was measured at 48 hours and 96 hours post treatment. The TOD measures the amount of persulfate that has reacted during the test time periods and provides information on the amount of persulfate required for oxidation. At each time interval, persulfate TOD, pH, and dissolved metals (filtered through a 0.45-μm filter) where measured. For testing, soil was exposed to each treatment at a 1:1 ratio of soil weight to liquid volume. This provided enough liquid to conduct the dissolved metals testing. Treated samples were sealed in amber jars and allowed to react on the laboratory bench at ambient temperatures. Dissolved metals were tested on a Thermo Scientific iCAP 6300 ICP.

Results for Soil 1 are shown in Tables 5 and 7. Results for Soil 2 are shown in Tables 6 and 8.

TABLE 5

Total Metals for Soil 1, mg/kg wet wt.

| Metal | Total, mg/kg wet wt. | Metal | Total, mg/kg wet wt. |
|---|---|---|---|
| Ag | 1.47 | Cu | 28.3 |
| Al | 4,620 | Fe | 5,090 |
| As | 1.50 | Mn | 119 |
| Ba | 68.5 | Ni | 6.60 |
| Be | 0.24 | Pb | 30.7 |
| Cd | 0.70 | Se | <0.66 |
| Co | 1.86 | V | 4.45 |
| Cr | 7.51 | Zn | 56.3 |

TABLE 6

Total Metals for Soil 2, mg/kg wet wt.

| Metal | Total, mg/kg wet wt. | Metal | Total, mg/kg wet wt. |
|---|---|---|---|
| Ag | 3.65 | Cu | 7.28 |
| Al | 170,000 | Fe | 1,150 |
| As | 1.89 | Mn | 2.36 |
| Ba | 6.70 | Ni | 3.02 |
| Be | 0.049 | Pb | 4.69 |
| Cd | 1.99 | Se | 0.91 |
| Co | 3.30 | V | 1.62 |
| Cr | 1.82 | Zn | 0.36 |

TABLE 7

Soil 1 Persulfate TOD, pH, and Dissolved Metals

|   |   | 1X NaOH | | 1X Mg(OH)$_2$ | | 1X Mg(OH)$_2$/P | | 1X In-Situ Mg(OH)$_2$ | |
| --- | --- | --- | --- | --- | --- | --- | --- | --- | --- |
|   |   | 48 Hr | 96 Hr | 48 Hr | 96 Hr | 48 Hr | 96 Hr | 48 Hr | 96 Hr |
|   | Persulfate TOD g/kg | 6.9 | 7.8 | 4.4 | 7.2 | 4.7 | 7.7 | 9.1 | 9.9 |
|   | Residual Persulfate g/kg | 3.1 | 2.2 | 5.6 | 2.8 | 5.3 | 2.3 | 0.9 | 0.1 |
|   | pH S.U. | 11.83 | 10.93 | 10.35 | 10.12 | 10.56 | 10.42 | 10.41 | 10.39 |
| ug/L | Ag | <5.0 | <5.0 | <5.0 | <5.0 | <5.0 | <5.0 | <5.0 | <5.0 |
|   | Al | 6,450 | 515 | 216 | <100 | 455 | <100 | 108 | <100 |
|   | As | 192 | 203 | <30 | <30 | <30 | <30 | <30 | <30 |
|   | Ba | 84 | 160 | 74 | 69 | 178 | 91 | 152 | 73 |
|   | Be | <1.0 | <1.0 | <1.0 | <1.0 | <1.0 | <1.0 | <1.0 | <1.0 |
|   | Cd | 3.1 | 3.5 | <3.0 | <3.0 | <3.0 | <3.0 | <3.0 | <3.0 |
|   | Co | <5.0 | <5.0 | <5.0 | <5.0 | <5.0 | <5.0 | <5.0 | <5.0 |
|   | Cr | 130 | 131 | 18 | 28 | 24 | 23 | 39 | 31 |
|   | Cu | 650 | 560 | 5.8 | 48 | 8.9 | 6.0 | 40 | 98 |
|   | Fe | 1,720 | 112 | 80 | 35 | 170 | 13 | 30 | 11 |
|   | Mn | 28 | 14 | 2.4 | <1.0 | 5.6 | <1.0 | 2.8 | <1.0 |
|   | Ni | 42 | 38 | <5.0 | <5.0 | <5.0 | <5.0 | <5.0 | <5.0 |
|   | Pb | 249 | 80 | <30 | <30 | <30 | <30 | <30 | <30 |
|   | Se | <30 | <30 | <30 | <30 | <30 | <30 | <30 | <30 |
|   | V | 221 | 235 | 5.0 | 24 | 6.4 | 8.1 | 6.1 | 8.3 |
|   | Zn | 107 | 130 | 3.4 | 18 | 5.3 | 8.0 | 64 | 80 |

|   |   | 3X NaOH | | 3X Mg(OH)$_2$ | | 3X Mg(OH)$_2$/P | | 3X In-Situ Mg(OH)$_2$ | |
| --- | --- | --- | --- | --- | --- | --- | --- | --- | --- |
|   |   | 48 Hr | 96 Hr | 48 Hr | 96 Hr | 48 Hr | 96 Hr | 48 Hr | 96 Hr |
|   | Persulfate TOD g/kg | 8.2 | >10 | 4.6 | 7.7 | 5.6 | 9.2 | 8.1 | >10 |
|   | Residual Persulfate g/kg | 1.8 | ND | 5.4 | 2.3 | 4.4 | 0.8 | 1.9 | ND |
|   | pH S.U. | 12.40 | 12.22 | 10.35 | 10.18 | 10.55 | 10.37 | 10.48 | 10.31 |
| ug/L | Ag | <5.0 | <5.0 | <5.0 | 7.4 | <5.0 | <5.0 | <5.0 | <5.0 |
|   | Al | 25,400 | 7,190 | 319 | <100 | 453 | <100 | 1,270 | <100 |
|   | As | 237 | 240 | <30 | <30 | <30 | <30 | <30 | <30 |
|   | Ba | 71 | 50 | 81 | 62 | 160 | 71 | 80 | 76 |
|   | Be | <1.0 | <1.0 | <1.0 | <1.0 | <1.0 | <1.0 | <1.0 | <1.0 |
|   | Cd | 3.5 | 3.4 | <3.0 | <3.0 | <3.0 | <3.0 | <3.0 | <3.0 |
|   | Co | <5.0 | <5.0 | <5.0 | <5.0 | <5.0 | <5.0 | <5.0 | <5.0 |
|   | Cr | 140 | 131 | 13 | 15 | 19 | 14 | 25 | 16 |
|   | Cu | 803 | 857 | 10 | 7.3 | 6.0 | 5.0 | 20 | 22 |
|   | Fe | 227 | 159 | 90 | 10 | 133 | 10 | 344 | 31 |
|   | Mn | 25 | 14 | 2.7 | <1.0 | 4.5 | <1.0 | 7.9 | <1.0 |
|   | Ni | 60 | 65 | <5.0 | <5.0 | <5.0 | <5.0 | <5.0 | <5.0 |
|   | Pb | 488 | 88 | <30 | <30 | <30 | <30 | <30 | <30 |
|   | Se | <30 | <30 | <30 | <30 | <30 | <30 | <30 | <30 |
|   | V | 218 | 215 | 5.1 | 8.4 | 6.5 | 8.7 | 6.5 | 8.8 |
|   | Zn | 130 | 83 | 4.9 | <3.0 | 4.7 | 3.1 | 18 | 49 |

TABLE 8

Soil 2 Persulfate TOD, pH, and Dissolved Metals

|   | 1X NaOH | | 1X Mg(OH)$_2$ | | 1X Mg(OH)$_2$/P | | 1X In-Situ Mg(OH)$_2$ | |
| --- | --- | --- | --- | --- | --- | --- | --- | --- |
|   | 48 Hr | 96 Hr | 48 Hr | 96 Hr | 48 Hr | 96 Hr | 48 Hr | 96 Hr |
| Persulfate TOD g/kg | >10 | >10 | 8.1 | >10 | 8.6 | >10 | 9.6 | >10 |
| Residual Persulfate g/kg | ND | ND | 1.9 | ND | 1.4 | ND | 0.4 | ND |
| pH S.U. | 10.93 | 10.07 | 10.12 | 10.12 | 10.41 | 10.42 | 10.25 | 10.29 |

TABLE 8-continued

Soil 2 Persulfate TOD, pH, and Dissolved Metals

| ug/L | | | | | | | | | |
|---|---|---|---|---|---|---|---|---|---|
| | Ag | <5.0 | 24.9 | <5.0 | <5.0 | <5.0 | <5.0 | <5.0 | 6.2 |
| | Al | 3,300 | 510 | 1,730 | <100 | 628 | <100 | 2,840 | <100 |
| | As | 254 | 154 | <30 | <30 | <30 | <30 | <30 | <30 |
| | Ba | 87 | 115 | 36 | 44 | 102 | 49 | 172 | 86 |
| | Be | 2.0 | 3.3 | <1.0 | <1.0 | <1.0 | <1.0 | <1.0 | <1.0 |
| | Cd | 3.2 | 1.5 | <3.0 | <3.0 | <3.0 | <3.0 | <3.0 | <3.0 |
| | Co | 18 | 33.4 | <5.0 | <5.0 | <5.0 | <5.0 | <5.0 | <5.0 |
| | Cr | 79 | 81.4 | 11 | <10 | 12 | <10 | 29 | <10 |
| | Cu | 94 | 102 | 5.4 | 20 | <5.0 | 11 | 5.3 | 7.7 |
| | Fe | 426 | 738 | 138 | 45 | 111 | 10 | 208 | 10 |
| | Mn | 13 | 16.8 | <1.0 | 1.4 | <1.0 | 1.3 | 2.1 | <1.0 |
| | Ni | 80 | 136 | <5.0 | <5.0 | <5.0 | <5.0 | <5.0 | 7.8 |
| | Pb | 261 | 51.6 | <30 | <30 | <30 | <30 | <30 | <30 |
| | Se | 30 | <30 | <30 | <30 | <30 | <30 | <30 | <30 |
| | V | 867 | 473 | 12 | 7.5 | 16 | 14 | 11 | 12 |
| | Zn | 124 | 193 | 7.6 | 21 | 6.0 | 17 | 35 | 41 |

| | | 3X NaOH | | 3X Mg(OH)$_2$ | | 3X Mg(OH)$_2$/P | | 3X In-Situ Mg(OH)$_2$ | |
|---|---|---|---|---|---|---|---|---|---|
| | | 48 Hr | 96 Hr | 48 Hr | 96 Hr | 48 Hr | 96 Hr | 48 Hr | 96 Hr |
| | Persulfate TOD g/kg | >10 | >10 | 7.8 | >10 | 7.7 | >10 | 8.2 | >10 |
| | Residual Persulfate g/kg | ND | ND | 2.2 | ND | 2.3 | ND | 1.8 | ND |
| | pH S.U. | 12.38 | 12.40 | 10.13 | 10.11 | 10.37 | 10.37 | 10.25 | 10.25 |
| ug/L | Ag | <5.0 | 7.9 | <5.0 | 7.4 | <5.0 | <5.0 | <5.0 | <5.0 |
| | Al | 29,400 | 17,300 | 628 | 267 | 629 | <100 | 2,300 | <100 |
| | As | 440 | 689 | <30 | <30 | <30 | <30 | <30 | <30 |
| | Ba | 235 | 74 | 35 | 43 | 35 | 57 | 53 | 100 |
| | Be | 1.5 | 2.6 | <1.0 | <1.0 | <1.0 | <1.0 | <1.0 | <1.0 |
| | Cd | 4.9 | 10 | <3.0 | <3.0 | <3.0 | <3.0 | <3.0 | 3.3 |
| | Co | 13 | 31 | <5.0 | <5.0 | <5.0 | <5.0 | <5.0 | <5.0 |
| | Cr | 111 | 207 | <10 | <10 | <10 | <10 | <10 | <10 |
| | Cu | 101 | 469 | <5.0 | 18 | <5.0 | <5.0 | <5.0 | 12 |
| | Fe | 528 | 2,100 | 80 | 94 | 80 | 14 | 144 | 16 |
| | Mn | 12 | 20 | <1.0 | 1.6 | <1.0 | <1.0 | <1.0 | 45 |
| | Ni | 65 | 202 | <5.0 | 8.0 | <5.0 | <5.0 | <5.0 | <5.0 |
| | Pb | 843 | 297 | <30 | <30 | <30 | <30 | <30 | <30 |
| | Se | 31 | 83 | <30 | <30 | <30 | <30 | <30 | <30 |
| | V | 1,260 | 1,800 | 14 | 27 | 14 | 12 | 20 | 7.8 |
| | Zn | 145 | 381 | 9.0 | 20 | 9.0 | 10 | 13 | NA |

The final pH of each treatment was greater than 10, thereby meeting the criteria of a hydroxide concentration of $1 \times 10^{-4}$ M assuming all of the alkalinity is as hydroxide (Tables 7 and 8). Where the persulfate TOD is reported as >10 g/kg, this means all of the SPS was utilized within the time frame of the test. As such, the final pH should be near 10 since the total alkalinity added was the amount required to increase the soil pH to ≈10.5 and account for sulfuric acid formation from the decomposition of SPS. Since SPS completely reacted in many tests (TOD>10), then the formation of sulfuric acid was complete, and by design, the final pH should be near 10.5.

As previously outlined, the amount of alkaline agent added was 1× and 3× the amount required to neutralize the acidity of the soil and SPS decomposition. As shown in Tables 7 and 8, the 1× alkaline addition tests had pH values near 10.5 after 96 hours. Furthermore, most if not all of the SPS was utilized within 96 hours; therefore a pH near 10.5 is expected. Higher pH levels for NaOH additions where observed at 48 hours and when the NaOH addition was 3× the required alkalinity. At 48 hours, higher pH levels associated with NaOH at 1× the required amount is due to SPS not completely reacting; sulfuric acid has not formed. Therefore, excess NaOH is present, resulting in higher pH values. The 3× NaOH requirement illustrates systems where the alkaline agent is added in excess of the total acidity, resulting in pH levels >12 (Tables 7 and 8).

When a magnesium based alkaline agent, Mg(OH)$_2$, is added in 1× and 3× the required acidity, the pH remains constant (Tables 7 and 8). This is due to the lower solubility of magnesium alkaline agents where the pH of such agents is 10.35 at saturation. Regardless of the amount of magnesium alkaline agent added, a pH of ≈10.35 was observed (Tables 7 and 8), providing the necessary amount of alkalinity to neutralize soil and SPS acidity. As noted earlier, the total hydroxide concentration was the same regardless of the alkaline agent tested.

Using a lower soluble alkaline agent (MgOH)$_2$) has a major advantage over more soluble alkaline agents (NaOH, Ca(OH)$_2$) where pH levels of >12 are achieved. The advantage is clearly observed with mobilization of metals, in particular amphoteric metals. Tables 7 and 8 show dissolved metals concentrations using varying alkaline agents. Amphoteric metals are shown in bold. As the pH increases, the mobilization of amphoteric metals is observed. In all cases, amphoteric metals concentrations were higher in NaOH based alkaline agents than magnesium alkaline agents. This was observed at both the 1× and 3× NaOH conditions, with higher concentrations at the 3× amount. Depending on the metal, significant increases were observed when the pH reached 12 or greater; in some cases (e.g., Al, Cr, Cu, Pb, V, Zn) levels of magnitude increased. Many of the amphoteric metals were below detection when magnesium-based alkaline agents were used. Arsenic showed a significant increase with the NaOH alkaline agent at both the 1× and 3× amounts while the 1× and 3× amounts of magnesium-based alkaline agent was below detection of 30 μg/L in both cases.

Higher pH levels mobilize metals and the higher the pH level, the greater the mobilized metal concentrations. In high pH conditions, metal concentrations can easily exceed background levels and may exceed regulatory levels. In sites that contain mixed wastes, such as both organic and metals contaminants, this can be especially problematic. Using magnesium-based alkaline agents has the following advantages.

1. Generates a hydroxide concentration that is effective in alkaline activating oxidants. The addition of additional precipitating metals, such as calcium, sequesters carbonates and improves the effectiveness of oxidants—see Table 4.
2. Lowers the pH to minimize mobilization of metals while at the same time maintains a total alkalinity to neutralize acidity from the soil and oxidant. In fact, magnesium alkaline agents can be added in significantly excess amounts and the pH will never obtain a level where metals mobilize.
3. Alkaline magnesium agents can be generated in-situ, eliminating slurry applications that may have implementation limitations.

More soluble alkaline agents (NaOH, $Ca(OH)_2$) have the following disadvantages.

1. Will increase the pH to >12, mobilizing metals from the system causing secondary metals contamination. A summary of sites treated with an ISCO application found 57% of the sites found higher metal concentrations during and after the ISCO application (Siegrist et. al., 2011). The duration of higher metal concentration ranged from one month to 36 months, and in two cases, the metal concentrations increased outside of the treatment zone. Assuming metals are eventually attenuated, waiting months to years for metal concentrations to return to baseline can delay site closure and increase the total project cost.
2. If the alkaline agent is added in excess of the total alkalinity, pH levels of >12 will be maintained and amphoteric metals will be mobilized.
3. If SPS is used as a oxidant and the amount of SPS added is in excess of the amount required for oxidation, high pH levels will be observed since the part of the alkaline agent dosage is based on the SPS concertation and the breakdown of SPS to form sulfuric acid. If all of the SPS doesn't decompose, then sulfuric acid will not be produced and excess alkaline agent will be present, increasing pH levels.

REFERENCES

Bossmann S H, Oliveros E, Gob S, Siegwart S, Dahlen E O, Payawan L, Straub M, Worner M, Braun A M. 1998. New evidence against hydroxyl radicals as reactive intermediates in the thermal and photochemically enhanced Fenton reaction. J Phys Chem A 102:5542-5550.

Buxton G V, Greenstock C L, Heiman W P, Ross A B. 1988. Critical reviews of rate constants for reactions of hydrated electrons, hydrogen atoms and hydroxyl radicals ($^-OH/^-O^-$) in aqueous solution. J Phys Chem Ref Data 17:513-886.

Chenju Liang, Zih-Sin W, Nihar M. 2006. Influences of carbonate and chloride ions on persulfate oxidation of trichloroethylene at 20° C. Sci of the Tot Environment. 370: 271-277.

Haselow, J, S., Siegrist, R, L., Crimi, M., and Jarosch, T. 2003. Estimating the Total Oxidant Demand for In Situ Chemical Oxidation Design. Remediation Autumn 2003.

House D A. 1962. Kinetics and mechanism of oxidations by peroxydisulfate. Chem Rev 62:185-203.

Huie R E, Clifton C L, Neta. P. 1991. Electron transfer reaction rates and equilibria of the carbonate and sulfate radical anions. Int J Rap Appl Instrum C Radiat Phys Chem 38:477-481

Huling S G, Arnold, R G, Sierka R A, Miller M R. 1998. Measurement of hydrowyl radical activity in a soil slurry using the spin trap a-(4-Pyridyl-1-oxide)-N-tert-butylnitrone. Environ. Sci. Technology 32: 3436-3441.

Krembs, F J. 2008. Critical Analysis of the Field-Scaled Application of In Situ Chemical Oxidation for the Remediation of Contaminated Groundwater. M S Thesis, Colorado School of Mines, Golder C O.

Kolthoff I M, Miller I K. 1951. The chemistry of persulfate. I. The kinetics and mechanism of the decomposition of the persulfate ion in aqueous medium. J Am Chem Soc 73:3055-9.

Lee H, A Park, Colin O. 2000. Stability of hydrogen peroxide in sodium carbonate solutions. TAPPI J. Peer Review Paper.

Lide D R. 2006. Handbook of Chemistry and Physics. CRC Press. Taylor and Francis Group, Boca Raton, Fla.

Liang C J, Huang S C. 2012. Kinetic model for sulfate/hydroxyl radical oxidation of methylene blue in a thermally-activated persulfate system at various pH and temperatures. Sustain. Environ. Res., 22(4), 199-208.

Mehrab M, Anderson W, Murray M., 2001. Photocatalytic degradation of aqueous organic solvents in the presence of hydroxyl radical scavengers. Inter. J. of Photenergy, Vol 3.

Neta P, Madhavan V, Zemel H, Fessenden R. 1977. Rate constants and mechanism of reaction of SO4—with aromatic compounds. J Am Chem Soc 99:163-4.

Osgerby I T. 2011. Site Characterization for ISCO Projects. NEWMOA Workshop, Mar. 15, 2011. www.newmoa.org/cleanup/cwm/isco/pres/Osgerby.pdf PeroxyChem. Activating Klozur® S P with a 25% Sodium Hydroxide Solution. www.peroxychem.com/media/191078/peroxychem-klozur-sp-activation-guide-alkaline-25.pdf Satoh A Y, Trosko, J E, Masten, S J. 2007. Methylene Blue Dye Test for Rapid Qualitative Detection of Hydroxyl Radicals Formed in a Fenton's Reaction Aqueous Solution. Environ. Sci. Technology 41: 2881-2887.

Siegrist R. L., Crimi, M., and Simpkin, T. J. in-Situ Chemical Oxidation for Groundwater Remediation. Springer Science+Business Media. 2011, Pg 348.

Staehelin J, Hoigné J. 1982. Decomposition of ozone in water: Rate of initiation by hydroxide ions and hydrogen peroxide. Environ. Sci. Technology 16: 676-681.

Wenzel, A D. 2012. Influence of ISCO Catalysts, Activators, and Chelators on Secondary Metals Mobility in Soil & Groundwater. RE3 Conference, Nov. 13, 2012.

Zuo Z, Cai Z, Katsumura Y, Chitose N, Muroya Y. 1999. Reinvestigation of the acid-base equilibrium of the (bi)

carbonate radical and pH dependence of its reactivity with inorganic reactants. Radiat Phys Chem 55:15-23.

U.S. Pat. No. 5,037,479.
U.S. Pat. No. 5,104,550.
U.S. Pat. No. 5,202,033.
U.S. Pat. No. 6,019,548.
U.S. Pat. No. 6,254,312.
U.S. Pat. No. 6,268,205.
U.S. Pat. No. 6,543,964.
U.S. Pat. No. 6,768,205.
U.S. Pat. No. 6,843,617.
U.S. Pat. No. 7,524,141.
U.S. Pat. No. 7,576,254.
U.S. Pat. No. 7,828,974.
U.S. Pat. No. 8,147,694.
U.S. Pat. No. 9,126,245.
U.S. Pat. No. 9,221,669

VERSIONS OF THE INVENTION

Exemplary versions of the invention are as follows:

1. A method of oxidizing an organic compound in a substrate, the method comprising treating the substrate at a hydroxide concentration of about $1 \times 10^{-4}$ M or greater with:
   an oxidant capable of producing free radicals in an amount sufficient to oxidize carbon in the substrate; and
   a first metal, wherein the first metal is a metal wherein a carbonate thereof has a lower solubility product constant than a hydroxide thereof, wherein the first compound is added to the substrate in an amount sufficient to precipitate carbonate from the substrate.

2. The method of version 1, wherein the first metal is an alkaline earth metal.

3. The method of any prior version, wherein the first metal is selected from the group consisting of calcium, strontium, and barium.

4. The method of any prior version, wherein the first metal is calcium.

5. The method of any prior version, wherein the treating comprises adding an oxide, hydroxide, or peroxide of the first metal or a combination thereof in an amount sufficient to yield a total hydroxide concentration of about $1 \times 10^{-4}$ M or greater in the substrate.

6. The method of any prior version, comprising adding the oxidant simultaneously with the first metal.

7. The method of any prior version, wherein the treating comprises adding a salt of the first metal.

8. The method of version 7, wherein the salt of the first metal is selected from the group consisting of a basic salt and a neutral salt.

9. The method of any one of versions 7-8, wherein the salt of the first metal is a neutral salt.

10. The method of any one of versions 7-9, wherein the salt of the first metal comprises a counterion selected from the group consisting of acetate, arsenide, azide, bromide, carbide, chlorate, chromate, chloride, chlorite, citrate, cyanamide, cyanate, cyanide, dichromate, dihydrogen phosphate, fluoride, gluconate, hydrogen sulfate, hydrogen sulfide, hydride, hypochlorite, lactate, glycerophosphate, isocyanate, iodate, iodide, monohydrogen phosphate, nitrate, nitride, nitrite, oxalate, perchlorate, permanganate, phosphate, phosphide, phosphite, selenide, silicate, sulfate, sulfide, sulfite, thiocyanate, and thiosulfate.

11. The method of any one of versions 7-10, wherein the salt of the first metal comprises a counterion selected from the group consisting of a sulfate, a sulfide, and a phosphate.

12. The method of any one of versions 7-11, wherein the treating comprises adding an oxide, hydroxide, or peroxide of a second metal or a combination thereof in an amount sufficient to yield a total hydroxide concentration of about $1 \times 10^{-4}$ M or greater in the substrate.

13. The method of version 12, wherein the second metal is the same as the first metal.

14. The method of any one of versions 12-13, wherein the second metal is selected from the group consisting of calcium, strontium, and barium and the first metal is selected from the group consisting of calcium, strontium, and barium.

15. The method of version 12, wherein the second metal is a metal other than the first metal.

16. The method of version 15, wherein the second metal is selected from the group consisting of a Group 1 metal, magnesium, and manganese.

17. The method of any one of versions 15-16, wherein the second metal is magnesium.

18. The method of any one of versions 7-17, wherein the treating further comprises adding to the substrate a magnesium salt, a sulfate salt distinct from the salt of the first metal, a phosphate salt distinct from the salt of the first metal, an iron salt, or any combination thereof.

19. The method of any one of versions 7-18, comprising adding the oxidant simultaneously with the salt of the first metal.

20. The method of any one of versions 1-6, wherein the treating comprises treating the substrate with a first composition and a second, separate composition, wherein:
   the first composition comprises a salt of a first composition metal selected from the group consisting of the first metal, magnesium, and manganese; and
   the second composition comprises an oxide, hydroxide, peroxide or combination thereof in an amount sufficient to yield a total hydroxide concentration of about $1 \times 10^{-4}$ M or greater in the substrate.

21. The method of version 20, wherein the first composition comprises the first composition metal in an amount greater than a stoichiometric amount to form a hydroxide from the oxide, hydroxide, peroxide or combination thereof in the second composition.

22. The method of version 20, wherein the first composition comprises the first metal in an amount greater than a stoichiometric amount sufficient to form a hydroxide from the oxide, hydroxide, peroxide or combination thereof in the second composition.

23. The method of version 20, wherein the first composition comprises the magnesium and/or manganese in an amount greater than a stoichiometric amount sufficient to form a hydroxide from the oxide, hydroxide, peroxide or combination thereof in the second composition.

24. The method of any one of versions 20-23, wherein the salt of the first composition metal comprises a counterion selected from the group consisting of acetate, arsenide, azide, bromide, carbide, chlorate, chromate, chloride, chlorite, citrate, cyanamide, cyanate, cyanide, dichromate, dihydrogen phosphate, fluoride, gluconate, hydrogen sulfate, hydrogen sulfide, hydride, hypochlorite, lactate, glycerophosphate, isocyanate, iodate, iodide, monohydrogen phosphate, nitrate, nitride, nitrite, oxalate, perchlorate, permanganate, phosphate, phosphide, phosphite, selenide, silicate, sulfate, sulfide, sulfite, thiocyanate, and thiosulfate.

25. The method of any one of versions 20-24, wherein the salt of the first composition metal comprises a counterion selected from the group consisting of a sulfate and a phosphate.

26. The method of any one of versions 20-25, wherein the oxide, hydroxide, peroxide, or combination thereof is an oxide, hydroxide, or peroxide of a second metal or a combination thereof, wherein the second metal is a metal other than the first metal.

27. The method of version 26, wherein the second metal is a Group 1 metal.

28. The method of any one of versions 20-27, wherein the treating further comprises adding to the substrate a magnesium salt, a sulfate salt distinct from the salt of the first metal, a phosphate salt distinct from the salt of the first metal, an iron salt, or any combination thereof.

29. The method of any one of versions 20-28, wherein the first composition, the second composition, or both the first composition and the second composition comprise the oxidant.

30. The method of any one of versions 20-29, wherein the treating the substrate with the first composition and the treating the substrate with the second composition occur simultaneously.

31. The method of any one of versions 20-29, wherein the treating the substrate with the first composition and the treating the substrate with the second composition occur sequentially.

32. The method of any prior version, wherein the substrate is treated with an amount of the first metal sufficient to maintain a concentration of an ionic form of the first metal in the substrate equal to or greater than a concentration of total carbonate and bicarbonate ion in the substrate.

33. The method of any prior version, wherein the oxidant is selected from the group consisting of a persulfate, a percarbonate, and a peroxide.

34. The method of any prior version, wherein the oxidant comprises permanganate.

35. The method of any one of versions 1-32, wherein the oxidant comprises permanganate in combination with any one or more of persulfate, a percarbonate, a peroxide, and ozone.

36. The method of any prior version, wherein the oxidant comprises a persulfate.

37. The method of any prior version, wherein the substrate is selected from the group consisting of a solid substrate and a liquid substrate.

38. The method of any prior version, wherein the substrate comprises a solid substrate.

39. The method of any prior version, wherein the substrate comprises a soil.

40. The method of any prior version, wherein the treating excludes adding calcium hydroxide.

41. The method of any prior version, wherein the treating excludes adding calcium hydroxide, potassium hydroxide, and sodium hydroxide.

What is claimed is:

1. A method of oxidizing an organic compound in a substrate, the method comprising treating the substrate at a hydroxide concentration of about $1 \times 10^{-4}$ M or greater with:
    an oxidant capable of producing free radicals in an amount sufficient to oxidize carbon in the substrate; and
    a first metal, wherein the first metal is a metal wherein a carbonate thereof has a lower solubility product constant than a hydroxide thereof, wherein the first metal is added to the substrate in an amount sufficient to precipitate carbonate from the substrate, wherein the substrate is treated with an amount of the first metal sufficient to maintain a concentration of an ionic form of the first metal in the substrate equal to or greater than a concentration of total carbonate and bicarbonate ion in the substrate.

2. The method of claim 1, wherein the first metal is an alkaline earth metal.

3. The method of claim 1, wherein the first metal is selected from the group consisting of calcium, strontium, and barium.

4. The method of claim 1, wherein the first metal is calcium.

5. The method of claim 1, wherein the treating comprises adding an oxide, hydroxide, or peroxide of the first metal or a combination thereof in an amount sufficient to yield a total hydroxide concentration of about $1 \times 10^{-4}$ M or greater in the substrate.

6. The method of claim 1, comprising adding the oxidant simultaneously with the first metal.

7. The method of claim 1, wherein the treating comprises adding a salt of the first metal.

8. The method of claim 7, wherein the salt of the first metal is selected from the group consisting of a basic salt and a neutral salt.

9. The method of claim 7, wherein the salt of the first metal is a neutral salt.

10. The method of claim 7, wherein the salt of the first metal comprises a counterion selected from the group consisting of acetate, arsenide, azide, bromide, carbide, chlorate, chromate, chloride, chlorite, citrate, cyanamide, cyanate, cyanide, dichromate, dihydrogen phosphate, fluoride, gluconate, hydrogen sulfate, hydrogen sulfide, hydride, hypochlorite, lactate, glycerophosphate, isocyanate, iodate, iodide, monohydrogen phosphate, nitrate, nitride, nitrite, oxalate, perchlorate, permanganate, phosphate, phosphide, phosphite, selenide, silicate, sulfate, sulfide, sulfite, thiocyanate, and thiosulfate.

11. The method of claim 7, wherein the salt of the first metal comprises a counterion selected from the group consisting of a chloride, a nitrate, a sulfate, and a phosphate.

12. The method of claim 7, wherein the treating comprises adding an oxide, hydroxide, or peroxide of a second metal or a combination thereof in an amount sufficient to yield a total hydroxide concentration of about $1 \times 10^{-4}$ M or greater in the substrate.

13. The method of claim 12, wherein the second metal is the same as the first metal.

14. The method of claim 12, wherein the second metal is selected from the group consisting of calcium, strontium, and barium and the first metal is selected from the group consisting of calcium, strontium, and barium.

15. The method of claim 12, wherein the second metal is a metal other than the first metal.

16. The method of claim 15, wherein the second metal is selected from the group consisting of a Group 1 metal, magnesium, and manganese.

17. The method of claim 15, wherein the second metal is magnesium.

18. The method of claim 7, wherein the treating further comprises adding to the substrate a magnesium salt, a sulfate salt distinct from the salt of the first metal, a phosphate salt distinct from the salt of the first metal, an iron salt, or any combination thereof.

19. The method of claim 7, comprising adding the oxidant simultaneously with the salt of the first metal.

20. The method of claim 1, wherein the treating comprises treating the substrate with a first composition and a second, separate composition, wherein:

the first composition comprises a salt of a first composition metal selected from the group consisting of the first metal, magnesium, and manganese; and the second composition comprises an oxide, hydroxide, peroxide or combination thereof in an amount sufficient to yield a total hydroxide concentration of about $1 \times 10^{-4}$ M or greater in the substrate.

21. The method of claim 20, wherein the first composition comprises the first composition metal in an amount greater than a stoichiometric amount to form a hydroxide from the oxide, hydroxide, peroxide or combination thereof in the second composition.

22. The method of claim 20, wherein the first composition comprises the first metal in an amount greater than a stoichiometric amount sufficient to form a hydroxide from the oxide, hydroxide, peroxide or combination thereof in the second composition.

23. The method of claim 20, wherein the first composition comprises the magnesium and/or manganese in an amount greater than a stoichiometric amount sufficient to form a hydroxide from the oxide, hydroxide, peroxide or combination thereof in the second composition.

24. The method of claim 20, wherein the salt of the first composition metal comprises a counterion selected from the group consisting of acetate, arsenide, azide, bromide, carbide, chlorate, chromate, chloride, chlorite, citrate, cyanamide, cyanate, cyanide, dichromate, dihydrogen phosphate, fluoride, gluconate, hydrogen sulfate, hydrogen sulfide, hydride, hypochlorite, lactate, glycerophosphate, isocyanate, iodate, iodide, monohydrogen phosphate, nitrate, nitride, nitrite, oxalate, perchlorate, permanganate, phosphate, phosphide, phosphite, selenide, silicate, sulfate, sulfide, sulfite, thiocyanate, and thiosulfate.

25. The method of claim 20, wherein the salt of the first composition metal comprises a counterion selected from the group consisting of a chloride, a nitrate, a sulfate and a phosphate.

26. The method of claim 20, wherein the oxide, hydroxide, peroxide, or combination thereof is an oxide, hydroxide, or peroxide of a second metal or a combination thereof, wherein the second metal is a metal other than the first metal.

27. The method of claim 26, wherein the second metal is a Group 1 metal.

28. The method of claim 20, wherein the treating further comprises adding to the substrate a magnesium salt, a sulfate salt distinct from the salt of the first metal, a phosphate salt distinct from the salt of the first metal, an iron salt, or any combination thereof.

29. The method of claim 20, wherein the first composition, the second composition, or both the first composition and the second composition comprise the oxidant.

30. The method of claim 20, wherein the treating the substrate with the first composition and the treating the substrate with the second composition occur simultaneously.

31. The method of claim 20, wherein the treating the substrate with the first composition and the treating the substrate with the second composition occur sequentially.

32. The method of claim 1, wherein the oxidant is selected from the group consisting of a persulfate, a percarbonate, and a peroxide.

33. The method of claim 1, wherein the oxidant comprises permanganate.

34. The method of claim 1, wherein the oxidant comprises permanganate in combination with any one or more of persulfate, a percarbonate, a peroxide, and ozone.

35. The method of claim 1, wherein the oxidant comprises a persulfate.

36. The method of claim 1, wherein the substrate is selected from the group consisting of a solid substrate and a liquid substrate.

37. The method of claim 1, wherein the substrate comprises a solid substrate.

38. The method of claim 1, wherein the substrate comprises a soil.

39. A method of oxidizing an organic compound in a substrate, the method comprising treating the substrate at a hydroxide concentration of about $1 \times 10^{-4}$ M or greater with:

an oxidant capable of producing free radicals in an amount sufficient to oxidize carbon in the substrate; and a neutral salt of a first metal, wherein the first metal is a metal wherein a carbonate thereof has a lower solubility product constant than a hydroxide thereof, wherein the first metal is added to the substrate in an amount sufficient to precipitate carbonate from the substrate.

40. A method of oxidizing an organic compound in a substrate, the method comprising treating the substrate at a hydroxide concentration of about $1 \times 10^{-4}$ M or greater with:

an oxidant capable of producing free radicals in an amount sufficient to oxidize carbon in the substrate; and a salt of a first metal, wherein the first metal is a metal wherein a carbonate thereof has a lower solubility product constant than a hydroxide thereof, wherein the first metal is added to the substrate in an amount sufficient to precipitate carbonate from the substrate, wherein the salt of the first metal comprises a counterion selected from the group consisting of acetate, arsenide, azide, bromide, carbide, chlorate, chromate, chloride, chlorite, citrate, cyanamide, cyanate, cyanide, dichromate, dihydrogen phosphate, fluoride, gluconate, hydrogen sulfate, hydrogen sulfide, hydride, hypochlorite, lactate, glycerophosphate, isocyanate, iodate, iodide, monohydrogen phosphate, nitrate, nitride, nitrite, oxalate, perchlorate, permanganate, phosphate, phosphide, phosphite, selenide, silicate, sulfate, sulfide, sulfite, thiocyanate, and thiosulfate.

41. The method of claim 40, wherein the salt of the first metal comprises a counterion selected from the group consisting of acetate, bromide, chloride, citrate, dihydrogen phosphate, gluconate, lactate, glycerophosphate, monohydrogen phosphate, nitrate, permanganate, phosphate, silicate, and sulfate.

42. The method of claim 40, wherein the salt of the first metal comprises a counterion selected from the group consisting of a chloride, a nitrate, a sulfate, and a phosphate.

43. A method of oxidizing an organic compound in a substrate, the method comprising treating the substrate at a hydroxide concentration of about $1 \times 10^{-4}$ M or greater with:

an oxidant capable of producing free radicals in an amount sufficient to oxidize carbon in the substrate;

a salt of a first metal, wherein the first metal is a metal wherein a carbonate thereof has a lower solubility product constant than a hydroxide thereof, wherein the first metal is added to the substrate in an amount sufficient to precipitate carbonate from the substrate, wherein the first metal is selected from the group consisting of calcium, strontium, and barium; and an oxide, hydroxide, or peroxide of a second metal or a combination thereof in an amount sufficient to yield a total hydroxide concentration of about $1 \times 10^{-4}$ M or greater in the substrate, wherein the second metal is selected from the group consisting of calcium, strontium, and barium.

44. A method of oxidizing an organic compound in a substrate, the method comprising treating the substrate at a hydroxide concentration of about $1\times10^{-4}$ M or greater with:
- an oxidant capable of producing free radicals in an amount sufficient to oxidize carbon in the substrate;
- a salt of a first metal, wherein the first metal is a metal wherein a carbonate thereof has a lower solubility product constant than a hydroxide thereof, wherein the first metal is added to the substrate in an amount sufficient to precipitate carbonate from the substrate; and
- an oxide, hydroxide, or peroxide of a second metal or a combination thereof in an amount sufficient to yield a total hydroxide concentration of about $1\times10^{-4}$ M or greater in the substrate, wherein the second metal is a metal other than the first metal, and wherein the second metal is magnesium.

\* \* \* \* \*